(12) United States Patent
Gutsell et al.

(10) Patent No.: US 10,006,867 B2
(45) Date of Patent: Jun. 26, 2018

(54) DEVICE AND APPARATUS

(71) Applicant: The Secretary of State for Environment, Food and Rural Affairs, Addlestone, Surrey (GB)

(72) Inventors: Graham Gutsell, Addlestone (GB); Philip Wakeley, Addlestone (GB)

(73) Assignee: The Secretary of State of Environment, Food and Rural Affairs, acting through the Animal and Plant Health Agency., Addlestone, Surrey (GB)

( * ) Notice: Subject to any disclaimer, the term of this patent is extended or adjusted under 35 U.S.C. 154(b) by 141 days.

(21) Appl. No.: 14/649,126

(22) PCT Filed: Dec. 3, 2013

(86) PCT No.: PCT/GB2013/053192
§ 371 (c)(1),
(2) Date: Jun. 2, 2015

(87) PCT Pub. No.: WO2014/087149
PCT Pub. Date: Jun. 12, 2014

(65) Prior Publication Data
US 2015/0346105 A1    Dec. 3, 2015

(30) Foreign Application Priority Data

Dec. 3, 2012   (GB) .................................. 1221726.1

(51) Int. Cl.
*B01L 1/00*     (2006.01)
*B01L 3/00*     (2006.01)
(Continued)

(52) U.S. Cl.
CPC ............ *G01N 21/78* (2013.01); *B01L 3/5023* (2013.01); *B01L 7/52* (2013.01); *B01L 2200/026* (2013.01);
(Continued)

(58) Field of Classification Search
CPC ......... B01L 2200/06; B01L 2200/0642; B01L 2300/087; B01L 2200/0689; B01L 2400/0475; B01L 2400/0487
See application file for complete search history.

(56) References Cited

U.S. PATENT DOCUMENTS 6,410,275 B1 *   6/2002   Kluttz .................... B01L 3/502
                                                            422/550
6,431,476 B1 *   8/2002   Taylor .................... B01L 3/502
                                                            241/1
(Continued)

FOREIGN PATENT DOCUMENTS

GB    2483858 A       3/2012
WO    9822625 A1      5/1998
(Continued)

OTHER PUBLICATIONS

UK Intellectual Property Office, Search Report, from Corresponding Application No. GB1221726.1, dated Jun. 6, 2013.
(Continued)

*Primary Examiner* — Nathan A Bowers
(74) *Attorney, Agent, or Firm* — Stites & Harbison, PLLC; David W. Nagle, Jr.

(57) ABSTRACT

There is provided a device (1) for carrying out an assay to detect a target nucleic acid in a sample, the device (1) comprising a body in which is formed: •a) a sample entry well location comprising a sample entry well (22) or means for engaging with a sample entry well (22), the sample entry well (22) having a first volume; •b) an amplification well
(Continued)

location comprising an amplification well (56) or means for engaging with an amplification well (56), the well (56) having a second volume less than or the same as the first volume and in which a nucleic acid amplification reaction of the target nucleic acid may be effected; •c) a first channel (60) linking the sample entry well (22) with the amplification well (56); •d) a diluent well location comprising a diluent well (35) or means for engaging with a diluent well (35), the well (35) being sealed, having a third volume greater than the second volume and being openable to an unsealed configuration; •e) a second channel (65) linking the diluent well (35), when in an unsealed configuration, with the amplification well (56); •f) a third channel (70) extending from the amplification well (56); and •g) a lateral flow device (80) arranged to receive sample from the third channel (70) and detect the target nucleic acid therein.

21 Claims, 10 Drawing Sheets

(51) Int. Cl.
  G01N 21/78 (2006.01)
  B01L 7/00 (2006.01)
  G01N 21/77 (2006.01)
(52) U.S. Cl.
  CPC ..... *B01L 2200/028* (2013.01); *B01L 2200/04* (2013.01); *B01L 2200/0684* (2013.01); *B01L 2200/0689* (2013.01); *B01L 2200/10* (2013.01); *B01L 2200/141* (2013.01); *B01L 2200/16* (2013.01); *B01L 2300/043* (2013.01); *B01L 2300/0672* (2013.01); *B01L 2300/0816* (2013.01); *B01L 2300/0825* (2013.01); *B01L 2300/0867* (2013.01); *B01L 2300/0883* (2013.01); *B01L 2300/1827* (2013.01); *B01L 2300/1844* (2013.01); *B01L 2400/049* (2013.01); *B01L 2400/0481* (2013.01); *B01L 2400/0487* (2013.01); *B01L 2400/0655* (2013.01); *G01N 2021/7759* (2013.01)

(56) References Cited

U.S. PATENT DOCUMENTS

| 2004/0110167 | A1  | 6/2004  | Gerdes et al. |
| 2005/0119589 | A1* | 6/2005  | Tung .................. A61B 10/0045 600/584 |
| 2010/0035349 | A1  | 2/2010  | Bau et al. |
| 2011/0039261 | A1  | 2/2011  | Hillebrand et al. |
| 2012/0270225 | A1  | 10/2012 | Wakeley et al. |

FOREIGN PATENT DOCUMENTS

| WO | 03076661   | A1 | 9/2003  |
| WO | 2004065010 | A2 | 8/2004  |
| WO | 2007116298 | A2 | 10/2007 |
| WO | 2008076395 | A2 | 6/2008  |
| WO | 2008105814 | A2 | 9/2008  |
| WO | 2011051735 | A2 | 5/2011  |

OTHER PUBLICATIONS

The International Bureau of WIPO, International Preliminary Report on Patentability, from Corresponding International Application No. PCT/GB2013/053192, dated Jun. 9, 2015.

Zhang, David Y., et al., Ramification Amplification: A Novel Isothermal DNA Amplification Method, Molecular Diagnosis, vol. 6, No. 2, 2001.

* cited by examiner

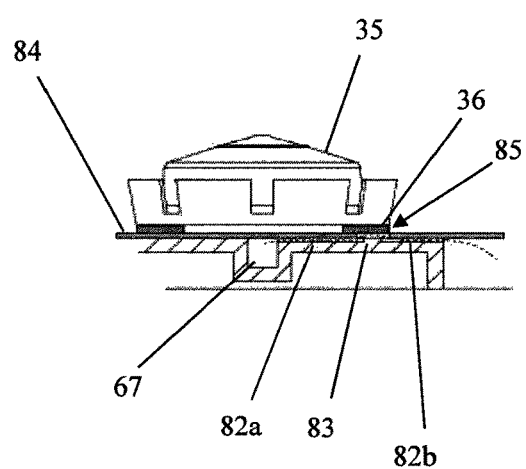
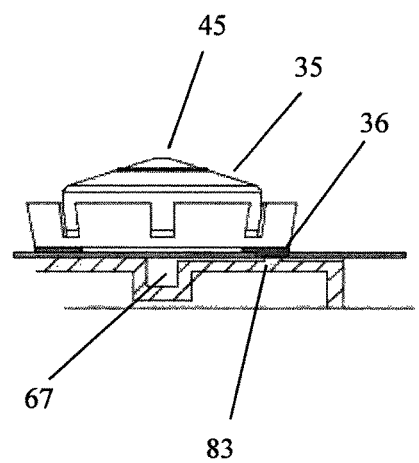
Figure 4C
Figure 4D

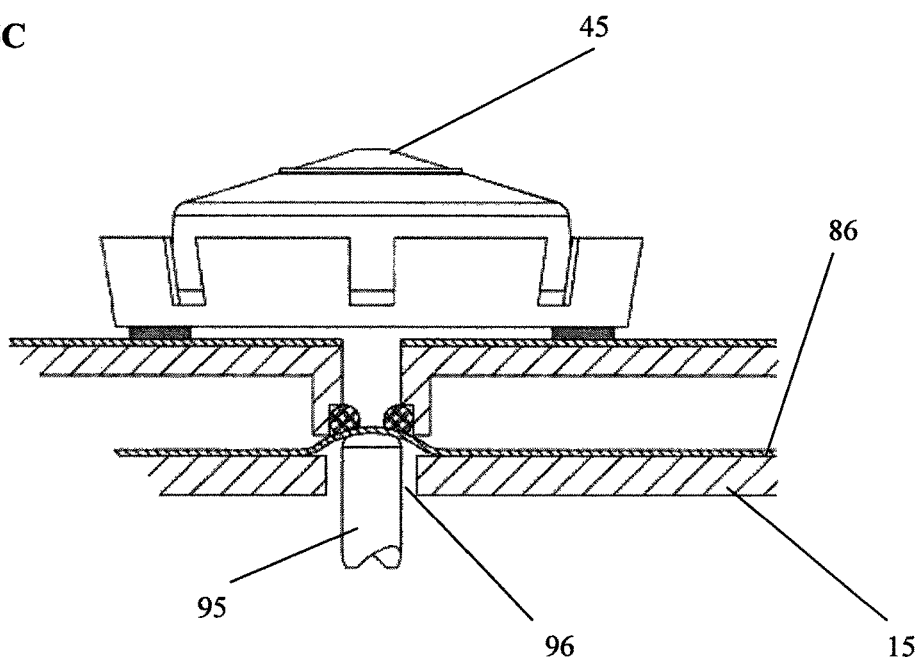

DEVICE AND APPARATUS

CROSS-REFERENCE TO RELATED APPLICATIONS

The present application is a national stage filing of International Patent Application No. PCT/GB2013/053192 filed on Dec. 3, 2013, which claims the benefit of priority to British Patent Application No. 1221726.1 filed on Dec. 3, 2012. The full contents of the International Patent Application are incorporated herein by reference.

FIELD OF THE INVENTION

The present invention relates to apparatus and systems for use in carrying out and detecting the products of chemical or biochemical reactions, for example, the detection of nucleic acids in samples such as biological samples, as well as to devices or combinations of devices, in particular disposable units for use in such apparatus and systems.

BACKGROUND

The detection of nucleic acids in samples, in particular biological samples, is well known in the fields of research, diagnosis (in particular of disease and genetic conditions), forensics and detection of microorganisms (for example for hygiene, environmental monitoring or threat reduction, where potentially harmful microorganisms such as bacteria are required to be detected rapidly).

Lateral flow devices (LFDs) have long been used in the field of diagnostics to detect target analytes such as proteins including hormones, antigens, antibodies etc. In these devices, a liquid sample containing or suspected of containing the analyte flows along a membrane, where it encounters labels, labelled binding partners and/or immobilised binding partners, in a sequence whereby a detectable visible signal is developed on the membrane depending on the presence or absence of the analyte in the sample.

The volume of liquid required to cause a sample to effectively flow along an LFD is generally quite significant. The membrane used as a substrate for the LFD is porous and will generally absorb significant amounts of liquid. Furthermore, the liquid flow must be sufficient to ensure that the labelled moieties are carried through to the detection zone on the device.

LFDs may also be used to detect analytes that comprise nucleic acids such as RNA or DNA. In this case, the binding partners for the analytes will include oligonucleotides that hybridise to the specific target sequence or, alternatively, binding partners for binding agents that have been incorporated into the RNA or DNA, for instance during a preliminary amplification reaction. For instance, nucleic acid amplification reactions may also be used to incorporate a binding agent, such as biotin, into the target so as to facilitate capture in the detection zone. Where biotin has been incorporated into a target nucleic acid, the presence of streptavidin or anti-biotin antibodies in the detection zone on the LFD will result in capture of biotin-labelled target nucleic acids in the capture zone.

Labelling may be effected using either labelled probes that also hybridise, for instance, to the target sequence so as to produce a visible signal when the target becomes immobilised in the detection zone. Labelling may also be achieved by incorporating a label into the target sequence, for instance during an amplification reaction, where labelled primers are used to generate an intrinsically labelled product. Suitable labels are well known in the art; for example, there are chemical or biochemical labels such as fluorescent labels, which include, for instance, fluorescein or fluorescein derivatives, or cyanine dyes, or labels that may be detected enzymatically such as digoxigenin. Alternatively or additionally, labels may comprise particulate labels such as gold, silver, and latex beads or particles, which produce a visible signal directly. These may be arranged to interact with target nucleic acid in the detection zone. In order to achieve this, the particles themselves will be labelled, for example conjugated to, moieties that interact with the target nucleic acid (for example other nucleic acids that hybridise to the target nucleic acid), or they may be conjugated to a binding agent such as streptavidin, that interacts with a binding partner such as biotin, which has been incorporated into the target nucleic acid sequence.

In fact, in most cases, the concentration of target nucleic acid in a biological sample is low, certainly below that at which a visible signal may be generated directly on a LFD. Thus, as a preliminary step, amplification of the nucleic acid is generally required.

Nucleic acid amplification techniques are a powerful tool in this area. There are many techniques, some of which are carried out isothermally and some of which require thermal cycling such as the polymerase chain reaction, which allow very small amounts of target nucleic acid in a sample to be amplified to detectable levels.

However, the extreme sensitivity of these techniques means that they are very prone to contamination or cross-contamination. Even a very small amount of contaminating nucleic acid may be subject to amplification in these methods, leading to false positives.

Many attempts have been made to address this problem, focussing principally on ensuring that the sample is treated in an environment isolated from the amplification process, as far as possible. Thus, methods for carrying out an amplification reaction and detecting the amplification product in a homogenous reaction, where the reaction vessel does not have to be opened, have been developed.

For example, WO2004/065010 relates to a microfluidic system for isolation and amplification of DNA and detection of DNA on a lateral flow detection strip. DNA from lysed bacterial cells is captured on a solid substrate through which amplification reagents are pumped. Amplified DNA is then pumped over a lateral flow strip. The system requires relatively complex apparatus, since pumping of reagents is required. The user is required to pipette the various solutions needed during the process onto the card, which carries significant risks of contamination.

US2011/0039261 also relates to a test system for nucleic acid analysis, with amplification of DNA and detection of amplification products on a lateral flow test strip. Again, it is necessary for the sample to be transferred between different cavities in the device, by some pumping mechanism. Running buffer to facilitate the detection on the lateral flow device is added to the system after the amplification sample has been passed to the test strip.

There is a need for an integrated system that allows for analysis to be carried out rapidly using simple apparatus, such that a relatively unskilled user can operate the system without the need for onerous manual operations, with minimal contamination risk and with maximal efficiency.

The applicants have developed a device that allows chemical and biochemical reactions such as nucleic acid analysis to be carried out in an isolated unit, which may be disposable, with minimum contamination risk. Aspects of a similar device were described in WO2011/051735. Significant improvements have now been provided, with advantages as described herein.

SUMMARY OF THE INVENTION

According to a first aspect of the invention, there is provided a device for carrying out an assay to detect a target nucleic acid in a sample, the device comprising a body in which is formed:
  (i) a sample entry well location comprising a sample entry well or means for engaging with a sample entry well, the well having a first volume;
  (ii) an amplification well location comprising an amplification well or means for engaging with an amplification well, the well having a second volume less than or the same as the first volume and in which a nucleic acid amplification reaction of the target nucleic acid may be effected in the liquid phase;
  (iii) a first channel linking the sample entry well with the amplification well (for example, linking directly with no intervening wells and/or channels);
  (iv) a diluent well location comprising a diluent well or means for engaging with a diluent well, the well being sealed, having a third volume greater than the second volume and being openable to an unsealed configuration;
  (v) a second channel linking the diluent well, when in an unsealed configuration, with the amplification well;
  (vi) a third channel extending from the amplification well; and
  (vii) a lateral flow device arranged to receive sample from the third channel and detect the target nucleic acid therein.

Any or all of the sample entry well, amplification well and diluent well may be provided as an integral part of the device. Alternatively, each or all may be formed as a separate module which may be engaged with the device at the sample entry well location, amplification well location, or diluent well location, as appropriate. Most typically, only the diluent well is a separate module, with other wells being integral to the device.

The diluent well being "sealed" indicates that the interior of the well is not in flow communication with other parts of the device. A user may open the diluent well to the unsealed configuration during use.

The relative volumes of the various wells allow the sample to be transferred between wells via the channels using a simple "overflow" or differential pressure mechanism. This indicates that pressure changes, resulting from the introduction of a fluid into the device, cause any fluid already present therein to move through available channels to other locations within the device. This process is described more fully elsewhere herein.

The channels suitably may be enclosed within the device and isolated from the external environment. For example, the channels may be formed as grooves in the body of the device, being isolated from the exterior environment by way of a film sealed across the body surface, over the grooves. The channels may, alternatively or additionally, form tubes extending through the body or a portion of the device, for example linking a well or a groove formed in one surface of the device or a portion thereof to a well or a groove formed in another surface of the device or a portion thereof. Any combination of these suggested groove and/or tube arrangements may be employed.

The sample entry well is preferably closable once the sample has been added to it, for example by means of a lid (which may be in the form of, for example, a cap or plug), before the device has been positioned within an apparatus for the purposes of effecting an assay. Alternatively, the closing may be effected after the device has been positioned within the apparatus. The closing may be effected manually or by actuation of closing means within the apparatus. When the sample entry well, amplification well and diluent well are engaged with the body of the device and the sample well lid is closed, the device as a whole is "closed" or sealed, i.e., the wells and/or channels may be in communication with each other, but they are isolated from the exterior atmosphere. As mentioned above, prior to use the diluent well is also not in communication with other parts of the device.

The lid and sample entry well are mutually formed so as to be engageable with one another as outlined in more detail below so that, when the lid is used to close the sample entry well, typically by depressing the lid over and/or into the well, a known, precalculated and/or predetermined volume of the liquid contained within the well is forced into the first channel and on to enter the amplification well. Air which previously occupied the first channel and amplification well is free to escape from the device by means of the second channel, until such time as the diluent well is sealingly engaged with the device at the diluent well location, as described further below.

This design of sample entry well and lid provides a significant advantage in that a larger, undetermined and/or imprecise, volume of sample can be initially introduced into the sample entry well by a user. However, only a predetermined volume, suitable for processing in an amplification reaction, is then transferred to the amplification well, the predetermined volume being relatively precisely determined by the relative dimensions of the lid and well. This obviates the need for a precise volume of sample to be applied to the device initially; so long as the volume added by a user to the sample well matches or exceeds the volume to be transferred towards the amplification well, the mechanism provided by closing the lid ensures that the correct, predetermined, volume is transferred. This is extremely advantageous, since it has the result that the device can be used by a relatively unskilled technician and, in addition, can be operated quickly without the need for careful measurement of sample volumes.

In a particular embodiment, the sample entry well may comprise a first chamber having a first cross-sectional area and a second chamber having a second cross-sectional area. The cross-sectional areas are measured perpendicularly to the longitudinal axis of the sample entry well, which extends from the base of the well to the open mouth of the well. In some embodiments, the second cross-sectional area may be greater than the first cross-sectional area. The first chamber may have a smaller volume than the second chamber. Of course, the first chamber has a smaller volume than the total combined volume of the first and second chambers. The first and second chambers are in flow communication with one another, each forming a portion of the sample entry well. The first chamber may be formed by a side wall which may be formed in the shape of, for example, a cylindrical tube or a tube having a rectangular or square cross-section, also having a base wall forming one end (the lower end or base, in use) of the well. The second chamber may also be formed by a side wall which may be formed in the shape, for example, of a cylindrical tube or a tube having a rectangular or square cross-section, though it need not be the same shape as the first chamber. However, the precise geometric shape of the chambers is not critical, as will be understood by the skilled person. It must be formed so as to enable the introduction of a predetermined volume of the sample into the first channel and amplification well by the action of closing the lid, as outlined above and elsewhere herein.

Typically, when the device is in use, the first chamber may be located lower within the device than the second chamber (and/or may be located within a different portion of the overall device, as described in the specific description below) and may sit directly above the first chamber, so the longitudinal axis of the tube of the first chamber is in line (i.e., is colinear) with the longitudinal axis of the tube of the second chamber; when the device is in use, the axes are substantially vertical. The volume of the first chamber may be 20-100 µl, or 40-70 µl, or about 58 µl, 59 µl, 60 µl, 61 µl, 62 µl, 63 µl, 64 µl, 65 µl or 66 µl, for example about 63 µl. The cross-sectional area of the second chamber may, in some embodiments, be greater than the cross-sectional area of the first chamber.

The upper limit of the wall of the first chamber is joined to the lower limit of the wall of the second chamber by a linking wall which is engageable with the lid so as to sealingly separate the contents of the first chamber from the contents of the second chamber. The linking wall may, for example, take the form of a step or sloping shoulders (i.e., forming a portion of a cone) so that the cross-sectional area of the second chamber reduces to a lower cross-sectional area of the first chamber. Alternatively, the linking wall may form or comprise a stepped profile between the wall forming each of the first and second chambers, the well in the region of the linking wall then having a smaller cross-sectional area parallel to the cross-sectional areas of the first and second chambers, which cross-sectional areas may be the same or different. That is, the linking wall may form a neck or narrower region or passage between the first and second chambers. In a further alternative, the linking wall may have the same dimensions as the first chamber and the sealing separation may be achieved by engagement of a part of the lid with the linking wall, as described below. In these circumstances, the linking wall may not be a visibly separate region, but may be the upper portion of the wall of the first chamber.

The first channel which links the sample entry well and the amplification well extends from a wall of the first chamber, i.e., there is a first channel entry opening or aperture formed in a wall of the first chamber which provides access to the first channel. Ideally, as mentioned above, the first chamber is formed by a side wall and a base wall and the opening may be formed in the base wall or in the side wall at a location close to the base wall. That is, the channel opening may be formed in the bottom of the sample entry well. In some embodiments, the base wall of the first chamber may comprise a depression or funnel, within which the channel opening may be formed.

The lid of the sample entry well is formed with a protruding distal portion which is formed to have mating dimensions with the first chamber of the sample entry well. By "mating dimensions" is meant that, when the sample entry well is closed with the lid, the material of the protruding distal portion substantially, but not necessarily completely, fills the volume of the first chamber.

The difference between the volume of the first chamber prior to the entry of the protruding distal portion and the volume remaining in the first chamber after the complete entry of the protruding distal portion is the volume of liquid which is displaced through the first channel towards the amplification well. This volume, called herein the sample entry volume, is typically the total volume required for the amplification, plus the volume of the first channel between the sample entry well and the amplification well. The sample entry volume, therefore, exceeds the amplification volume. For example, the amplification volume may be approximately 25 µl and the volume of the first channel may be approximately 12 µl, so that the sample entry volume, displaced from the first chamber by the entry of the protruding distal portion of the lid, is approximately 37 µl. Appropriate relative dimensions of the first chamber and the protruding distal portion of the lid can be designed by the skilled person according to the use to which the device is to be put and the volume of liquid sample desired to be transferred into the device.

The terms "distal" and "proximal" in relation to the lid portions are used with reference to an external region of the lid which may be contacted by a user so as to use the lid to close the sample entry well, as described below. That is, the proximal portion of the lid is closest to the part of the lid with which the user (or apparatus operated by the user) typically makes contact to achieve closing of the well, whilst the distal portion is furthest away and is the portion which, in use, protrudes into the sample entry well, as described elsewhere herein. When the lid is closed, the distal portion sits within the first chamber of the sample entry well and the proximal portion sits within the second chamber.

The external surface of the protruding distal portion may ideally have an interference fit with the internal surface of the wall of the first chamber. This interference fit may be around the whole of the protruding distal portion, or a part thereof, for example by way of a circumferential sealing ring as described below. The proximal portion of the lid may be formed having non-mating dimensions with the second chamber of the sample entry well; that is, when the sample entry well is closed using the lid, the material of the proximal portion of the lid does not fill the volume of the second chamber. This provides the advantage that the lid of the sample entry well can be closed without significant overflow or splashing of sample from the sample entry well, because there is sufficient volume available in the second chamber, even when the lid is closed, for the portion of the sample which is not pushed into the first channel to remain within the well. There may also be provided a further overflow chamber linked to the second chamber and isolated from the remainder of the device, such that any liquid displaced by the closing of the lid can be diverted to the overflow chamber without a risk of contaminating other parts of the device.

In use, the lid may be closed in a two-step process. The protruding distal portion of the lid is initially inserted via the second chamber of the sample entry well to make sealing contact with the linking wall between the wall of the second chamber and the wall of the first chamber. This may be further facilitated by the provision of a tapered nose region of the protruding distal portion of the lid, to promote correct engagement of the distal portion with the linking wall. Alternatively or additionally, a sealing ring (such as, for example, a rubber or elastomeric O-ring) may be provided around a circumference (or outer wall, where the lid is not cylindrical) of the distal portion of the lid, to make sealing contact with the linking wall. The sealing contact between the distal portion of the lid and the linking wall isolates the sample liquid located within the first chamber from the sample liquid located within the second chamber. As outlined above, the structure of the proximal portion of the lid may be such that the displacement of liquid caused by the insertion of the distal portion into and through the second chamber can be accommodated without liquid exiting the sample entry well, or with liquid exiting only to the overflow chamber, when present.

The distal portion of the lid forms a sealing contact with the linking wall, for example via the sealing ring, so that, in the second step of the lid closing process, when the lid is further depressed to force the protruding distal portion into the first chamber to fill or substantially fill it, the liquid contained within the first chamber exits the sample entry well via the first channel entry opening, which is preferably located towards the bottom of the well, the volume of liquid displaced being sufficient that an amplification volume of sample is transferred through the first channel to the amplification well. The volume of displaced liquid may, as outlined above, be equal to the amplification volume plus the volume of the first channel. The amplification volume is a sample volume suitable for conducting a nucleic acid amplification reaction and may be, for example, 15-60 µl, 20-50 µl, typically about 23 µl, 24 µl, 25 µl, 26 µl or about 28 µl, ideally about 25 µl.

In an exemplary but non-limiting embodiment, as described in more detail elsewhere herein, the sample entry well is generally cylindrical, with the first chamber formed by a cylindrical tube having a first internal diameter and the second chamber formed by a cylindrical tube having a second internal diameter, the two chambers being joined by a sloping shoulder portion (i.e., a conical portion). The lid takes the form of a cylindrical bung dimensioned to provide an interference fit (for example, by way of a rubber or elastomeric O-ring formed around the circumference of the bung) within the first chamber when the lid is closed. The bung portion of the lid is joined at its proximal end to a circular plate or flange portion which has a diameter greater than the internal diameter of the second chamber of the sample entry well; furthermore, the bung is of a length so that, when the lid is fully closed, the most distal part of the bung reaches almost to the end or bottom region of the first chamber (but typically does not make contact with the end or bottom) and the side of the plate portion adjacent the bung is in contact with the top of the second chamber. The extent of travel of the distal part of the bung is limited by the abutment of the plate portion with the top surface of the device or with material surrounding the exterior or mouth of the second chamber. In consequence, when the lid is closed, the mouth of the sample entry well is covered by the plate portion. When the lid is closed, the material of the bung portion extends through the second chamber into the first chamber, with space being available around the bung material within the second chamber to accommodate sample which was not forced into the first channel (and on to the amplification chamber) when the lid was closed to substantially fill the volume of the first chamber.

However, the skilled person will understand that the same principle of transferring a precise, predetermined, volume of liquid to the amplification chamber can be achieved using geometric shapes other than cylinders. The critical features are that the external dimensions of the distal portion of the lid have mating dimensions with the internal dimensions of the first chamber of the sample entry well, achieving at least a partial interference fit, such that a defined volume of a sample contained in the first chamber of the sample entry well is forced out of the first chamber into the first channel towards the amplification chamber, by the action of closing the lid.

As mentioned, the device also comprises a diluent well suitable for containing diluent and connected to the amplification well by way of a second channel, wherein the second channel is arranged such that diluent from the diluent well may be transferred to the amplification well. The diluent well suitably may be pre-located at, or positionable at, a diluent well location, the well and the location initially being in a non-sealing relationship. That is, the diluent well can be non-sealingly engaged with the device at the diluent well location, for example so that air forced through the second channel in consequence of the closing of the sample entry well lid can escape to the exterior of the device. The diluent well location comprises a second channel entry opening which is thereby accessible to diluent dispensed from the diluent well, i.e., diluent flows into the second channel. Typically, in use, the diluent well is positioned over the second channel entry opening, in consequence of locating the diluent well at the diluent well location. To ensure that diluent flows into the second channel and cannot escape elsewhere, a diluent well seal is positioned between the mating faces of the diluent well and the diluent well location. The seal may be formed by a gasket, washer, O-ring or other compliant material located at one or both of the mating faces. Preferably, the seal is in the form of an annulus or ring that surrounds the second channel entry opening when the diluent well is in place at the diluent well location.

The diluent well location may comprise diluent well engagement means such that the diluent well can be clipped or otherwise securely positioned into place at the diluent well location. This allows the well to be held in place on the remainder of the device, but in a non-sealing relationship, so that air can escape as described above. In this configuration, engagement of the diluent well at the diluent well location does not compress the diluent well seal and a seal is not formed. This allows the second channel to remain open to the atmosphere until after the introduction of the sample, as described above. The diluent well may be moved so that the diluent well seal forms a seal, for example as a result of compression of the diluent well seal formed by a gasket, washer, O-ring or other compliant material, so that the diluent well is then in sealing engagement with the diluent well location. This compression may be achieved by insertion of the device into apparatus arranged to receive the device.

Since the amplification well has a smaller volume than the diluent well, as outlined further below, the linking of the diluent well to the amplification well by the second channel has the effect that the contents of the amplification well are "flushed through", via the third channel to the LFD. The liquid cannot leave the amplification well via the first channel, since it is a closed unvented volume in consequence of the seal provided by the closed lid of the sample entry well. This system means that the amplification reaction can be carried out in a small volume of liquid, which is preferable or even optimal for the amplification reaction. The amplification product may then be diluted and mixed sufficiently so that, at the point of arrival at the lateral flow device, it may flow freely along the lateral flow device, by addition of the diluent. Sufficient dilution may require, for example, a ratio of at least about 1:4 amplification volume: diluent volume as measured at the point of entry onto the lateral flow device, although this may require a greater initial amount of diluent fluid to be dispensed towards the amplification chamber. This is because, in the small volumes utilised within the device, fluids have a tendency not to mix within channels but to move sequentially through channels before mixing within larger volume wells. For example, where the amplification volume is about 25 µl, a volume in excess of about 125 µl of diluent should be delivered through the second channel into the amplification well. This volume fills the second channel and then transfers about 100 µl of diluent to the third channel, pushing the liquid from the amplification well ahead of it through the third channel towards the lateral flow device (and a mixing well, where present, as described below). This achieves a degree of dilution at the lateral flow device of 1:4, i.e., 25 µl amplification volume and 100 µl diluent, a total of 125 µl. 25 µl of diluent remains behind in the amplification well.

The diluent well typically contains preloaded diluent and is provided as a sealed container, to be opened only when diluents are required for use. Therefore, the diluent well is not in flow communication with any other part of the device until it is unsealed/opened. The sealing of the well may be achieved by means of a lid, cap, plug or seal (such as a film) formed across the mouth of the well. Thus, for instance, diluent may be contained within a sealed flexible pouch, blister pack or ampoule which forms the diluent well and may be accommodated within the device, supplied in contact with it, or supplied to be engaged with it at the diluent well location. There is typically provided means for opening the pouch or ampoule such as piercing means like a pin or cutter provided within the diluent well. The piercing means may also be formed as part of the body of the device, rather than forming part of the diluent well. In either case, the piercing means is arranged so that the diluent well is only punctured or opened (i.e., placed in fluid connection with the second channel) when pressure or force is applied to the container or the piercing means during the process of operation of the device. For instance, the diluent well may be formed as a deformable tray or vessel sealed with a film or lid formed across the mouth of the well, the external surface of the film or lid being placed in contact with the diluent well location of the device, when in use. When diluent is required (after the amplification reaction is complete), the body of the diluent vessel is depressed towards the film so that a piercing means formed within the body of the vessel is forced into piercing contact with the film at the required time, enabling liquid to flow into the second channel entry opening. Only then is the diluent well in flow communication with other parts of the device. Importantly, this utilisation of a sealed diluent well, opened only when diluent is required, prevents liquid diluent from prematurely contacting the membrane of the lateral flow device before it is used, which may cause the device to deteriorate so that it will not work correctly (if at all) and must be discarded.

Where the device is intended for engagement with an apparatus as discussed further below, the act of depressing the diluent well may be facilitated automatically by the apparatus. The depressing may be controlled so that diluent flows into the device over a period of time, for example over a period of around a few seconds. This may have advantages in that a controlled volume of diluent may be transferred into the device, in accordance with the ratio mentioned above of amplification volume:diluent volume. Typically, the diluent volume will be less than the volume of diluent contained in the diluent well before use. The volume of diluent transferred into the device will preferably be the diluent volume plus the volume of the second channel. For example, as described above, where the amplification volume is 25 µl, the diluent volume may be 100 µl, but the amount of diluent transferred into the device may be 125 µl, in order to achieve the required dilution at point of entry to (i.e., contact with) the lateral flow device. In an embodiment, the user or the apparatus may maintain the diluent well in the compressed configuration for at least a period of time, to avoid sucking liquid back through the device into the diluent well. Alternatively or additionally, depression of the well may be irreversible.

As mentioned above, the device may comprise one or more sealing film layers formed across at least a portion of a surface on or within the device, covering the channels when formed as grooves instead of tunnels. A sealing film layer may also sit between the surface of the LFD and the exterior of the device.

The diluent well location may comprise a closable air vent. This is in flow communication with the second channel. The air vent may be formed as an aperture within the material forming the second channel, for example, positioned at or close to the second channel entry opening. The air vent is not open to the exterior of the device as a whole, but to a void in the device located within the body of the device and/or between the body of the device and one or more film layers applied to the surface thereof, as described in more detail below. The term "void", in this context, is simply sufficient space, within the body of the device and/or between the one or more film layers and the surface of the body of the device, to contain a small volume of air displaced when the diluent well is moved from a non-sealing to a sealing engagement with the device, by pressing the diluent well into sealing engagement with the device. For example, air may be found within or under the diluent well seal, located between the mating faces of the diluent well and diluent well location.

Before the device is used, the air vent is in an open configuration, to enable the volume of air from within or under the diluent well seal to escape into the void when the diluent well is compressed into position at the diluent well location, moving the diluent well into sealing engagement with the remainder of the device, as described above. In the absence of the air vent, this volume of air would be driven into the second channel and could displace the sample from the amplification well; if this occurred prior to commencing the amplification reaction (as is typical if the diluent well is engaged with the remainder of the device prior to use), amplification would not occur. The air vent may then be moved to a closed configuration, such that further air or liquid cannot escape via this route.

By way of one non-limiting example, the air vent may be closed simultaneously with the action of depressing the diluent well to force diluent to enter the second channel. Preferably, however, the air vent is closed prior to the opening of the diluent well and introduction of diluent into the second channel. In an embodiment, the diluent well itself may comprise means for occluding the air vent. For example, as described elsewhere herein, pressure applied to the diluent well or a portion thereof may cause a portion of the diluent well seal to be forced into a sealing relationship with the material forming and/or surrounding the air vent, causing the vent to be blocked and providing the closed configuration of the vent. Suitable arrangements are described elsewhere herein.

In an alternative embodiment of the air vent, the air vent may be formed as an aperture in the base of the entry to the second channel, i.e., it is positioned directly under the second channel entry opening in the diluent well location, as described in more detail elsewhere. Therefore, as above, the air vent is in flow communication between the second channel and a void in the device, allowing air to escape into the void via the second channel when the diluent well is compressed into sealing engagement with its dispensing location. An air vent sealing member such as an O-ring may be positioned within the air vent aperture, in a non-sealing arrangement when the air vent is in the open configuration. The air vent sealing member may be moved to a sealing arrangement, for example by application of pressure against the sealing member to force it against the material of the body of the device, for example by actuation and engagement of an air vent closing member which may be operated by a user. The air vent closing member may be actuated automatically by an apparatus with which the device may be engaged.

In an embodiment of the device, the amplification well is provided as a separate module which, in use, is engaged with the device via a protrusion which is an amplification spigot. This is a protrusion from the body of the device, the spigot having side walls the exterior of which are dimensioned so as to be capable of frictional engagement with interior side walls of the amplification well, the spigot then extending into the well. The spigot has a distal end which protrudes furthest into the amplification well and a proximal end which is the end closest to the body of the device. Alternatively, the spigot may extend into an amplification well which is manufactured to form a part of the device, i.e., to not be a separate module.

The spigot comprises an exit opening from each of the first and second channels and an entry opening to the third channel. Therefore, liquid sample can be delivered to the amplification well via the first channel and liquid diluent can be delivered to the amplification well via the second channel. When liquid sample is initially dispensed from the sample entry well to the amplification well, air contained in the amplification well may escape via the second channel, being in flow communication with the air vent, as outlined above. As mentioned above, at the point when liquid diluent is dispensed in a volume greater than the volume of the amplification well, the air vent is in the closed configuration and the first channel is sealed because the sample entry well is already closed with the entry well lid, with the result that the liquid pushed from the amplification well by dispensing of the diluent has only one route of escape and is forced into the third channel via the third channel entry opening in the amplification spigot, moving on through the third channel towards the LFD.

The spigot may be formed as a non-uniform and/or non-unitary shape, with a first portion of the spigot (called herein the first spigot portion) protruding to a greater extent into the amplification well than a second spigot portion which protrudes to a lesser extent into the well than the first spigot portion. Typically, the exit opening from the first channel and the entry opening to the third channel may be formed in the first spigot portion, with the exit opening from the second channel being formed in the second spigot portion. Therefore, the first channel exit opening and the third channel entry opening are located towards the most distal end of the amplification spigot (or protrusion), with the second channel exit opening located towards a proximal region of the amplification spigot, since the first portion has a longer length and extends further into the amplification well than does the second portion. This arrangement has advantageously been found to improve the transfer of liquids through the device, avoiding the formation of blockages caused, most typically, by the undesirable formation of air bubbles within the well/channel system.

The second channel exit opening and the third channel entry opening are typically formed in the material of the spigot as an aperture or hole, having substantially the same cross-sectional area and shape as the cross-sectional area and shape of the channel to which the opening is linked. However, in the case of the first channel exit opening, it has been found advantageous to form the opening with a cross-sectional area greater than the cross-sectional area of the first channel. The first channel exit opening may be formed in the side wall and distal end of the first spigot portion, for example taking the form of an open spigot channel in the material of the side wall of the first spigot portion. The term "open channel" is used herein to explicitly refer to a channel which is not enclosed on all sides in a longitudinal direction. This has the result that at least a portion of the spigot channel is open so that fluid may emerge from the first channel at a location adjacent an internal side wall of the amplification well and flow down the side of the wall into the base of the well. This arrangement has been found, advantageously, to minimise the formation of bubbles within the well/channel system of the device and, therefore, to facilitate reliable filling of the amplification well, as well as onward movement of fluids into the third channel. An example of a suitable structure may be understood by reference to the specific description herein, though the skilled person may be able to envisage alternative arrangements. For example, the first channel exit opening may be formed as an aperture wholly positioned in the side wall of the first spigot portion, with none of the opening being formed in the distal end of the first spigot portion. In other words, the open spigot channel arrangement described herein is just one embodiment; others may be utilised so long as the object is achieved that sample fluid is delivered to the amplification well by at least a proportion of the fluid flowing down the sides of the amplification well.

As well as controlled delivery of liquid sample to the amplification well achieved by the location and formation of the first channel exit opening, the positioning of the third channel entry opening in the distal end of the first spigot portion, the distal end being located towards the base of the amplification well when the well is engaged with the device, has the result that fluid moves efficiently from the amplification well into the third channel when diluent is added to the amplification chamber via the second channel. As mentioned above, because liquid diluent is dispensed through the second channel in a volume greater than the volume of the amplification well, the liquid mixture is forced into the third channel via the third channel entry opening in the amplification spigot. The first channel is closed off by the closing of the sample entry well lid, so that liquid is obliged to move into the third channel. The liquid then moves on through the third channel to the LFD. There is sufficient space between the surface of the LFD and the sealing film layer that air in the third channel can escape and not prevent entry of liquid from the amplification well into the third channel. This process has been found to be improved when the third channel entry opening is formed in the distal end of the first spigot portion, positioned in use towards the base of the amplification well.

As with the arrangement of the spigot portions described above, these features advantageously assist with avoiding the formation of air bubbles in the well/channel system of the device.

Depending upon the volumes used, liquid passing along the third channel may be delivered directly onto a sample receiving section of a lateral flow device, which may comprise a wicking pad. In a preferred embodiment, where significant volumes are delivered via the third channel, it may be convenient to provide a mixing well arranged to receive liquid from the third channel before it reaches the LFD via the wicking pad, where present. This is because it has been found that, in view of the small amplification volume and the small cross-sectional area of the channels of the device, when diluent is added to the amplification well it tends to "push" the amplification volume ahead of it into the third channel, rather than mixing in the amplification well prior to moving as a mixture into the third channel. In such cases, the lateral flow device is advantageously arranged to receive sample from the mixing well. For instance, a receiving section of the lateral flow device may project into the mixing well. In addition to providing efficient mixing of the amplified material received from the amplification well with the diluent, this may also be convenient where the volumes being delivered are greater than can be conveniently or rapidly absorbed directly by a receiving section of the lateral flow device.

Thus, in a particular embodiment, the present invention provides an assembled device for carrying out an assay to detect a target nucleic acid in a sample, the device comprising
(i) a sample entry well into which a sample comprising a target nucleic acid may be loaded onto the device;
(ii) an amplification well, connected to the sample entry well by means of a first channel, in which a nucleic acid amplification reaction of the target nucleic acid may be effected in the liquid phase;
(iii) a lid engageable with the sample entry well so as to force a pre-determined volume of fluid via the first channel into the amplification well;
(iv) a diluent well connected to the amplification well by means of a second channel;
(v) a mixing well connected to the amplification well by means of a third channel, wherein the third channel is arranged such that contents of the amplification well may be transferred to the mixing well; and
(vi) a lateral flow device arranged to receive sample from the mixing well and detect the target nucleic acid therein.

The device of the invention may be a unitary device containing all the above elements in an integral unit or entity. For example, the elements of the device may all be contained within a single body or housing. However, in a particular embodiment, the device may be modular, in particular so that the diluent well (iv) may be provided as a separate unit that is attachable to (i.e., engageable with) the device for use. Likewise the amplification well (ii) may, alternatively or additionally, also be provided as a separate unit that is attachable to (i.e., engageable with) the device for use, preferably via an amplification spigot as described above. In such cases, the individual modules, one of which is a device as defined above but with receiving means for the diluent and/or amplification well instead of a diluent or amplification well, respectively, the other of which is a diluent well or amplification well, respectively, adapted for receipt into the receiving means, form further aspects of the invention. Such modular wells are suitably self-supporting and may be provided with annular flanges or lips so as to facilitate handling and attachment to the receiving means.

Therefore, an embodiment of the device comprises a body in which is formed:
(i) a sample entry well location comprising means for engaging with a sample entry well;
(ii) an amplification well location comprising means for engaging with an amplification well;
(iii) a first channel linking the sample entry well location with the amplification well location;
(iv) a diluent well location comprising means for engaging with a diluent well;
(v) a second channel linking the diluent well location with the amplification well location;
(vi) a third channel extending from the amplification well location, linking the amplification well location with
(vii) a lateral flow device;
characterised in that, when the sample entry well, amplification well and diluent well are engaged with the device, the device is sealed or "closed" as defined below. That is, the wells and channels are in communication with one another, but are isolated from the atmosphere. In an embodiment, the diluent well location may comprise an air vent, which is a vent between the diluent well and a void within the device, as discussed elsewhere herein.

In a particular embodiment of the device, it comprises a body in which is formed:
(i) a sample entry well location comprising a sample entry well having a first volume;
(ii) an amplification well location comprising an amplification well, the well having a second volume less than or the same as the first volume and in which a nucleic acid amplification reaction of the target nucleic acid may be effected in the liquid phase;
(iii) a first channel linking the sample entry well with the amplification well (for example, linking directly with no intervening wells and/or channels);
(iv) a diluent well location comprising means for engaging with a diluent well and an entry opening to
(v) a second channel linking the diluent well location with the amplification well;
(vi) a third channel extending from the amplification well; and
(vii) a lateral flow device arranged to receive sample from the third channel and detect the target nucleic acid therein.

The device preferably further comprises a sample entry well lid as described above. The device may additionally comprise an air vent at the diluent well location, which is a vent between the diluent well location and a void within the device, as discussed elsewhere herein.

The device described in this embodiment is optimised, by inclusion of the above features, to isolate sample added to the sample entry well from the exterior atmosphere after a lid (which may be integral or separate) is engaged with the sample entry well to close it, as described elsewhere. The liquid contained in the sealed diluent well is only introduced into the system when it is needed, preventing deterioration of the lateral flow device prior to use. The flow of diluent through the system enables the transfer of the contents of the amplification well in diluted form, in a suitable volume, to contact the lateral flow device. As mentioned elsewhere herein, the described combination of features provides a device which can be used accurately with a low risk of contamination, even by a relatively unskilled user.

As used herein, the term "lateral flow device" refers to any device that operates by the flow of liquid along a bibulous membrane. Thus, this includes conventional "dipsticks" which may be used vertically, as well as devices in which membranes are fixed in a horizontal position so that flow along the membrane occurs horizontally or laterally.

The term "channel" refers to a path defined in a solid body through which liquid can flow freely, for example under the influence of differential pressure and/or gravity, and in particular does not necessarily rely on capillary action. In most embodiments of channels mentioned herein, with the exception of the spigot channel, the channels linking wells are suitably tunnels or tubes, i.e., enclosed channels within the device, for example within a housing as described above. Alternatively, the channels may be manufactured as a groove in the body of the device, being closed by application of a sealing film across at least a portion of the body of the device as described above, such that the grooves are enclosed to form tunnels. Such a film may also cover the LFD and, in some embodiments, may be also utilised to provide a void enclosed between the film and the body of the material, as described elsewhere, to facilitate escape of air from channels of the device.

By combining sections in which liquid is transferred by bibulous flow with sections in which normal liquid flow is permitted within the same device, the device of the invention allows each stage of the assay (amplification and detection) to be carried out under the preferred conditions. Thus, the volume of any amplification reaction mixture in the amplification well may be selected so as to provide optimal amplification conditions. However, that volume may be changed and, in particular, increased by addition of diluent, facilitating transfer to the mixing well and subsequently to the lateral flow device so as to provide the preferred volumes for use in the lateral flow device. Transfer of liquid between the sections of bibulous and normal liquid flow is facilitated by the fact that the sections are contained within the same device and the transfer advantageously can be facilitated without exposing the contents of the device to the atmosphere or other external influences. Furthermore, the device is amenable for automatic or semi-automatic operation of the assay.

As used herein, the term "closed" means that the wells and/or channels are isolated from the atmosphere, although they may be in communication with each other. In the case of the diluent well, the term "closed" also indicates that it is isolated from other parts of the device, i.e., it is not in flow communication with any of the channels or other wells of the device. Similarly, the term "closable" refers to a well that may be isolated from the atmosphere (and from other parts of the device), for example by means of a lid, cap, plug or seal. This term may indicate, as in the case of the diluent well, that the well is in a closed configuration prior to use, but may be opened after the well is engaged with the device to allow liquid contained in the well to flow through channels and wells of the device. Therefore, the well is openable to form a flow communication with other parts of the device but, when used with the device in accordance with the present description, may never be opened to the atmosphere. The diluent well is not in the open configuration until after the air vent, where present, has been moved to the closed configuration, as described elsewhere herein.

In the case of modular devices, where the amplification and/or diluent well is provided as a separate but attachable element of the device, the device itself may provide the lid, cap, plug or seal of the well. In such instances, the device is provided with a suitable receiving means such as a projecting protrusion or spigot, that fits into the opening of the relevant well, for example by means of a snap or screw fit. In such cases, provision must be made in the attachable well to accommodate any channels entering or exiting the well so that they are not blocked by the walls of the well when it is in position in the device. This has been described in most detail above in relation to the amplification spigot which extends into the amplification well.

Where the mixing well is closed (e.g., by covering with a sealing film) and the third channel is also enclosed, amplification reactions can be conducted and the resultant amplification product subsequently transferred to a lateral flow device for detection without intervening exposure to the atmosphere, therefore minimising risk of contamination.

As mentioned above, the amplification well is of smaller volume to the diluent well and, where present, the mixing well. Furthermore, it is generally smaller in volume than the sample entry well. For example, the amplification well may have a capacity (or a capacity when engaged with the device, where the amplification well is provided separately to the remainder of the device) of from 10-250 µl such as from 15-50 µl, for example about 23 µl, 24 µl, 25 µl, 26 µl, 27 µl or about 28 µl, preferably about 25 µl, whereas the diluent and mixing wells suitably have capacities in the range of from 40-4000 µl, for instance from 40-2500 µl. In a particular embodiment, the diluent and mixing wells may have capacities of about 500 µl and 125 µl, respectively. The sample entry well may have a capacity of from 40-1000 µl, such as from 50-250 µl, for example about 100 µl. A smaller predetermined volume may be transferred from the sample entry well into the device by the closing of the lid, as described above. The diameter of the amplification well may, for example, be in the range of 4-5 mm (for example, about 4.7 mm), with a depth of about 4-10 mm, for example about 4.8 mm. Once engaged with the spigot of the device, the space between the distal end of the amplification spigot and the base of the amplification well may be in the range of 1-2 mm, for example about 1.5 mm, 1.6 mm, 1.7 mm or 1.8 mm.

In contrast, the diameter of the diluent and/or mixing wells may be in the range of 7-20 mm, for example about 12 mm, with a depth of about 5 mm. The mixing well is preferably in the form of a channel of relatively large cross-sectional area, preferably with some changes of its longitudinal axis along its length. This facilitates mixing, creating a "serpentine" shape to the well. For example, the mixing well may have cross-sectional dimensions of about 2 mm×3 mm and a length along the whole of its longitudinal axis (including changes of direction) of about 20 mm.

The sample entry, diluent and mixing wells may have the same volumes or their volumes may differ. Each has a volume greater than that of the amplification well. As mentioned above, the volume of liquid displaced from the first chamber of the sample entry well by the closing of the lid may be about 37 µl, where the amplification volume is about 25 µl and the volume of the first channel is about 12 µl. Since there is a volume remaining in the first chamber of the sample entry well after the lid has been inserted, the total volume of the first chamber is, therefore, greater than about 37 µl.

This arrangement means that the device is suitable for carrying out a range of chemical or biochemical reactions where the reaction itself is optimally effected in a relatively small volume of liquid, that volume being generally smaller than that required to effectively provide a signal on a conventional lateral flow device.

In particular embodiments, the mixing well may be formed in a non-circular shape. It may, for example, be formed in a generally serpentine shape, comprising at least two bends (i.e. changes in direction of the long axis of the well). The inventors have determined that forming the mixing well in such a way particularly facilitates mixing. In particular, when the diluent is moved from the diluent well via the amplification well, there is a tendency for the contents of the amplification well to be "pushed ahead" of the diluent as it flows through from the small volume second channel via the small volume amplification well and small volume third channel, to the mixing well. The serpentine shape of the mixing well encourages effective mixing of the liquid components which enter the well in this way, prior to making contact with the LFD. This improves the reliability of detection, reducing false positives and negatives. Ideally, the cross-sectional area of the mixing well is substantially greater than the cross-sectional area of the third channel.

The cross-sectional dimensions of the channels have been determined as optimal by the inventors, as a compromise between fluid flow behaviour and surface tensions at the walls of the wells. As such, they are large enough to discourage laminar flow in order to facilitate efficient mixing, but small enough to keep the volume of liquid intact and controlled, to ensure reliable delivery to the lateral flow device. Dimensions of about 2 mm×3 mm have been found to be ideal for the mixing well, with cross sectional dimensions of the other flow channels being generally about 0.3 mm×0.3 mm.

In some embodiments, the channels may have variations in their cross-sectional area along their length; for example, the first channel may comprise a section having a larger cross-sectional area at the end adjacent the sample entry well, to facilitate entry of the sample into the first well as the sample entry well lid is closed, as described above.

Preferred embodiments of such devices will operate in a similar manner to embodiments described herein, the membrane of the lateral flow device being loaded with appropriate detection reagents. Suitable chemical and biochemical reactions may comprise any form of chemical or biochemical reaction.

Suitably, the lateral flow device is fully enclosed within the overall device, for example it is encased within a housing of the device, also to minimise the risk of contamination. In this case, a viewing window is suitably provided in the device or housing to allow the results of the assay to be read, or the housing itself is of a transparent material at least in the region over the LFD.

The lateral flow device may be arranged so that the bibulous membrane projects into the mixing well and thus absorbs sample directly from the mixing well. In a particular embodiment however, a liquid flow element, in particular one or more wicking element(s), is arranged to receive sample from the mixing well and transfer it to a sample receiving section of the membrane of the lateral flow device. Suitable wicking elements include a pad of wicking fibre, for example constructed from a dense, hydrophilic fibrous material such as cellulose or the like. The wicking element or elements may project into or otherwise contact the mixing well at one end and make contact with an end region of the membrane of the lateral flow device at the other, to ensure that liquid transfers from the mixing well onto the membrane in an acceptable and controlled flow. In a particular embodiment, the wicking element lines at least a portion of the base of the mixing well so that liquid delivered into the well is applied directly to the wicking element.

The wicking element or elements may act as a reservoir for reagents used in the lateral flow device to develop a signal. For instance, binding partners for the amplified target nucleic acid which are suitably labelled as described above, may be stored within the wicking element. These are then transferred with the sample along the membrane of the lateral flow device to the appropriate detection zone on the membrane.

The device is suitably a disposable unit intended for single use. At least a part of the device may be contained within a housing which is suitably of a rigid plastics material. The housing may serve to enclose channels formed as grooves in the body of the device by covering the surface in which the grooves are formed.

The amplification well may be adapted to allow, specifically, a nucleic acid amplification reaction to be carried out therein. Such reactions are generally carried out in relatively small volumes and thus the volume of the amplification well will be relatively small, as discussed elsewhere herein.

In particular, however, the amplification well is suitably adapted to make it available for heating to the desired temperatures generally undertaken in a nucleic acid amplification reaction. Thus, the well is suitably constructed of a material which is tolerant of such temperatures and/or temperature fluctuations and changes that are involved in a typical nucleic acid amplification reaction, without the material deforming or degrading. A polypropylene material may be suitable, for example.

The amplification well can be heated or cooled in a controllable manner. Although heating elements such as resistive heating elements, or cooling elements or thermostat elements as well as temperature control or temperature measurement elements such as thermistors or thermocouples may be included within the device itself, in a particular embodiment, the first well is arranged to be adjacent to, in contact with or otherwise encompassed by such elements within an apparatus, adapted to accommodate the device for assay purposes. The device is suitably adapted to fit into the apparatus so that the first well may be subject to heating, ideally controlled heating.

In particular embodiments, the amplification well is arranged on a projection or limb of the device so that it is readily available for heating and/or cooling to effect a nucleic acid amplification, for example using external heating devices or, where appropriate, thermal cyclers. For example, the amplification well may extend outwardly of the housing, for instance on a projection as described above, so that it may be accommodated within a corresponding well within a heating or thermocycling element such as a block heater which optionally forms part of the apparatus. Alternatively, the projecting well may be arranged to fit within an air cooling or heating chamber of, for example, a forced air heater, thermal cycler or a thermostat. As mentioned above, the amplification well may be formed as a separate module, engageable with the device prior to use.

The device may include grooves, channels or other indentations, arranged so that heating or thermostat elements within the apparatus project into the device around or in the vicinity of the amplification well when the device is positioned within the apparatus, so as to allow the controlled heating of the contents of the first well.

Fluids are suitably transferable through the first and/or second and/or third channels under pneumatic, hydraulic or vacuum controlled flow. This is typically and advantageously achieved without the need for any external automated source of pneumatics, hydraulics or vacuum, but rather by the action of the simple movements and/or deformation of components of the device itself. For example, material may be transferred through the first channel, from the sample entry well to the amplification well, by the action of closing the lid of the sample entry well, as described above. Likewise, diluent may be transferred through the second channel, to pass through the amplification well with amplification product and diluent subsequently being transferred through the third channel, by the action of unsealing or opening the diluent well, as described above. The actuation of the lid and/or unsealing or opening of the diluent well (for example, by deforming the well) may be achieved directly by a user, or via automated means. However, it can be contemplated that, in some embodiments, the housing further comprises at least one pump port, each linked to any one of the sample entry, amplification or diluent wells. Each pump port normally may be sealed, but just before or on introduction of the device into an apparatus for carrying out the assay, it is opened and becomes connected to a kinetic energy source, for example, a source of hydraulic or pneumatic pressure or vacuum, that is able to drive the diluent from the well to which it is connected through a channel into a further well. A corresponding vent port, connected to the same well as each pump port, may be provided so as to allow liquid flow through the channel.

The channels themselves will be arranged to facilitate the necessary transfer. Thus, for example, the first channel may connect to the base of the sample entry well so that the sample can be removed from it, as described above. The first channel may enter the amplification well in a side region thereof, as described above. The third channel may be positioned near the base of the amplification well (for example, by way of the third channel entry opening being positioned at the distal end of the first portion of the amplification spigot) and connect to an upper region of the mixing well.

Since the diluent well is of greater capacity than the amplification well, diluent delivered into the amplification well will effectively overflow the amplification well, into the third channel and thence into the mixing well. Thus, the product of any amplification in the amplification well may be delivered in dilute form to the mixing well. Alternatively, delivery of diluent may serve to "push" the contents of the amplification well through the third channel ahead of the diluent, such that the majority of any mixing is not achieved until the amplification well contents and subsequent diluent reach the mixing well.

In general, an end region comprising the sample receiving zone of the membrane of the LFD will be located within the mixing well so that liquid containing any amplified nucleic acid is absorbed into the membrane and will wick along the length thereof. One or more detection or control zones, in which suitable binding partners for target moieties are immobilised, are provided on the membrane downstream of the sample receiving zone in the conventional manner, so that target nucleic acids are captured (or otherwise in the case of a competitive assay format) in the zone. The nucleic acids are suitably labelled either directly during the amplification reaction or by contact with a labelled probe, which is either introduced into the amplification reaction or moveably located on the LFD. Thus, accumulation of labelled material, for example, associated with particulate labels (e.g., latex beads) as described above in a detection zone, gives rise to a visible signal in the LFD. Examples of such devices are illustrated, for example, in US2004/0110167.

Suitable membranes may comprise cellulose based materials such as cellulose, nitrocellulose, or carboxymethylcellulose, hydrophilic polymers including synthetic hydrophilic polymers such as polyesters, polyamides, carbohydrate polymers, hydrophobic polymers such as halogenated polymers such as polytetrafluoroethylene, fibreglass or porous ceramics.

Particularly suitable membranes include cellulose membranes and in particular nitrocellulose membranes which may be laminated, such as those available from Millipore. These may be supported on a backing material such as a plastic backed membrane such as a polyester (Mylar®) or PET backed cellulose membrane.

The backing of such membranes are naturally hydrophobic whereas the cellulose itself is hydrophilic, which gives rise to the necessary wicking effect. However, the hydrophilicity can give rise to problems when these are used in the context of an immunoassay procedure. The membranes used in these devices may, if required, be blocked using conventional blocking agents. Blocking agents are those that may reduce non-specific interactions between any protein in the sample and the membrane or increase the wicking rate of the sample. They are generally applied after the application of immobilised binding agents and are usually selected from three types of agent including proteins, surfactants and synthetic polymers. Particular examples of proteins which may be used as blocking agents include bovine serum albumin (BSA), or non-fat dry milk components such as casein.

Suitable synthetic polymers for use as blocking reagents include polyvinyl alcohol (PVA), polyvinylpyrroline (PVP), polyethylene glycol (PEG) and polyoxyethylene fatty ethers such as those derived from lauryl, cetyl, stearyl and oleyl alcohols and sold under the trade name Brij™.

Surfactants may also be included, for example, non-ionic surfactants such as polyoxyethylene sorbitan monolaureate which is sold under the trade name of Tween™ 20 and octylphenol ethoxylates for example as sold by Dow as the Triton X™ series, for example Triton X-100.

It is generally recognised that mixtures of two or more of these types or classes of blocking reagent may be particularly employed, for example a mixture comprising a surfactant and a synthetic polymer as outlined above.

In a preferred embodiment however, no blocking agent is used on the membrane.

Reagents for carrying out the amplification, such as primers, enzymes, probes etc. may be preloaded into the amplification well so that it is ready to receive sample directly for amplification. In particular such reagents may be present in dried and in particular freeze dried form, to ensure that they do not decompose or react prematurely. This is especially convenient where the amplification well is provided as a separate module, engageable with the remainder of the device, typically by frictional engagement with an amplification spigot.

The sample may, if required and if a sample is available in a suitable form, be added directly to the sample entry well. However, in general, it is necessary to extract and purify nucleic acids from samples. Samples may be biological samples, for example, obtained from a human or animal. Detection of nucleic acids may also be a way of detecting the presence of micro-organisms in, for example, environmental water samples.

It is preferred that liquid components of the amplification reaction, such as the amplification buffer, are introduced into the amplification well only at the start of the amplification reaction. This minimises contamination risks and also prevents premature reactions occurring.

In order to achieve both of these objects, the sample may be introduced to the device in a liquid form which comprises extracted nucleic acids and the liquid components suitable for the amplification reaction, such as assay buffers. Therefore, prior to being added to the device, a sample may be pre-processed, for example to lyse microbiological cells in a sample and release target nucleic acid for detection. The target nucleic acid (with or without other components such as cellular debris) may be prepared in amplification buffer prior to being added to the sample entry well, the lid then being closed as described elsewhere.

Similarly, the apparatus will comprise heating means adapted to interact with the amplification well as described above in a manner which allows the desired amplification reaction to be carried out in the well. Heating means may be provided on all sides of the amplification well and/or at the bottom of the well and across the top of the well. For example, the amplification spigot and amplification well engaged with the spigot, when the device is in use, may be located on a portion of the device which protrudes from the remainder of the device, this protrusion being insertable into the apparatus at a location that allows the protruding portion of the device, comprising the amplification well, to be surrounded by or located adjacent to heating means.

Generally, it is preferable that the amplification reaction conducted is one of the many isothermal amplification reactions known in the art such as nucleic acid sequence based amplification (NASBA), strand displacement amplification (SDA), transcription mediated amplification (TMA), Loop-Mediated Isothermal Amplification (LAMP), Q-beta replicase and rolling circle amplification, 3SR, ramification amplification (as described by Zhang et al., Molecular Diagnosis (2001) vol. 6, p 141-150), recombinase polymerase amplification (available from TwistDx, Cambridge, UK) and others. This requires less complex heating arrangements than thermal cycling reactions such as polymerase chain reaction. However, it would be possible, if the apparatus included thermal cycling means, to carry out amplification reactions such as the polymerase chain reaction or ligase chain reaction, that require thermal cycling.

The processing apparatus may comprise diluent administration means which, when the device is in position within the apparatus, may engage with the diluent well when positioned at the diluent well location. The diluent administration means may be actuated so as to deform the diluent well to transfer diluent via the second channel entry opening into the amplification well. As described above, administration may be controlled by the apparatus so that diluent flows into the device over a period of time, for example over a period of around a few seconds, such as between 1-5 seconds, or 2-4 seconds. This may have advantages in that a controlled volume of diluent may be transferred into the device at a controlled rate.

The further advantage of utilising a diluent administration means is that it can be accurately configured so as to ensure that a predetermined required volume of diluent can be transferred through the second channel into the device, by way of calculation, for example, as to the extent to which a diluent well should be deformed in order to transfer a desired volume of diluent into the device. The configuration may be altered as appropriate for use with a particular device, since other variants such as materials used and the type of reaction to be carried out in the amplification well may alter the absolute volume of diluent to be administered. A further advantage may be that the engagement of the apparatus with the diluent well may be unaffected by dimensional variances in other portions of the device.

In some embodiments, as described above, the device may comprise an air vent. This may be moved from an open to a closed configuration by engagement of the diluent well with the device. As described in more detail below, in one embodiment the air vent may comprise an air vent channel extending from the opening of the second channel adjacent the diluent well location, the channel being divided into two portions by an air vent dividing wall. The diluent well may comprise a deformable gasket which, when the diluent well is in position at the diluent well location, makes non-sealing contact with the air vent dividing wall. The air vent is in an open configuration in this arrangement, with air able to flow from the first half air vent channel (which extends from the end of the air vent channel adjacent the opening of the second channel towards the air vent dividing wall), between the material of the wall and the material of the gasket, into the second half air vent channel and thereby into the body of the device surrounding the diluent well location. The air vent may be moved to the closed configuration by pressing the diluent well and, hence, the gasket, into sealing contact with the air vent dividing wall such that air is no longer able to flow out from the interior of the device via the first half air vent channel into the second half air vent channel. When the device is in position within the apparatus, this may be achieved by air vent sealing means, configured to apply pressure to at least a portion of the diluent well so to press the gasket into sealing contact with the air vent dividing wall. The air vent sealing means may be identical to or separate from the diluent administration means. Ideally, the air vent sealing means is actuated prior to actuation of the diluent administration means, such that the air vent is in the closed configuration prior to the opening of the diluent well and administration of diluent into the device via the second channel.

In an embodiment, where the diluent well is generally circular in shape, it may comprise an annular channel surrounding the circumference of the well. This may provide a position of engagement for an air vent sealing means formed by a hollow cylindrical tube member within the apparatus which can be actuated to push the diluent well, when positioned at the diluent well location, so that the gasket forms a seal against the air vent dividing wall. Such air vent sealing means may also be utilised to move the diluent will from an unsealed to a sealed engagement with the rest of the device. The diluent administration means may be formed by a cylindrical piston member having a smaller diameter than the internal diameter of the cylindrical tube member and extending through the cylindrical tube member to engage with the diluent well. The cylindrical piston member can then be actuated to deform the diluent well and dispense diluent into the device, as described above.

As outlined above, an alternative arrangement for the air vent comprises a sealing member moveable from non-sealing to a sealing configuration by application of pressure against the sealing member to force it against the material of the body of the device. This may be achieved, for example, by way of an O-ring positioned within the air vent, as described elsewhere herein.

Thus, in use, the device described above is loaded into apparatus adapted to receive it. Once in position in the apparatus, the various pneumatic or vacuum ports, if provided in the device, become connected to the pneumatic, hydraulic or vacuum system of the apparatus. Alternatively or additionally, the diluent administration means engages with the diluent well and, at an appropriate time, is actuated to facilitate administration of diluent into the device. Likewise, the air vent sealing means may be arranged to contact the device so as to move the air vent from an open to a closed configuration. The air vent sealing means may, for example, be a cylindrical tube member within the apparatus which can be actuated to push the diluent well as described above. Alternatively, the air vent sealing means may be a rod or pin which can extend via an aperture in an exterior housing of the device to engage with a sealing member (such as an O-ring) as described above. In at least this embodiment, the air vent is isolated from the exterior of the device by a film layer formed between the exterior material and the sealing member. The air vent sealing means engages with the sealing member through the film, i.e., the film is disposed between the sealing means and the sealing member. Since the film is thin and flexible, it does not hinder the movement of the sealing means from a non-sealing to a sealing configuration.

In addition, controllable heating elements provided in the apparatus are able to interact with the amplification well for the purposes of carrying out a nucleic acid amplification reaction therein. The apparatus is suitably programmed to effect various stages of the process, including transferring liquids from one well to another and heating the amplification well automatically, in a sequence that ensures that nucleic acid is amplified and detected in a single operation.

Such apparatus forms a further aspect of the invention, as does a system comprising a device and apparatus as described above.

Thus, in a particular aspect, the invention further provides apparatus for carrying out a chemical or biochemical reaction and optionally detecting the product, in particular in an assay to detect a nucleic acid in a sample, the apparatus comprising:
(i) means for receiving a device as described above, preferably when the sample entry well lid is in the closed configuration, and
(ii) heating means arranged to controllably heat the amplification well so as to allow a nucleic acid amplification reaction to be carried out therein.

The apparatus may further comprise (iii) diluent administration means arranged to engage with the diluent well when the device is received in means (i), such that the diluent administration means can be actuated to cause diluent to be dispensed into the device. Alternatively or additionally, the device may further comprise (iv) air vent sealing means which may, in an embodiment, be arranged to engage with the diluent well, such that the air vent sealing means can be actuated to apply pressure to the diluent well so that the diluent well gasket forms a sealing contact with the air vent dividing wall. Diluent administration means and air vent sealing means may be identical such that diluent is dispersed and the air vent closed simultaneously. Alternatively, the air vent sealing means may interact with a sealing member which is independent of the diluent well and may be actuated to move the air vent to a closed configuration.

Where required, the apparatus may further comprise (v) a transport system, such as a pneumatic, hydraulic or vacuum system, connectable to the device so as to promote transfer of material between wells in the device.

The apparatus suitably further comprises a control system, such as computer or microcontroller system, that will effect the desired assay procedure automatically within the device, by controlling the heating means and, where present, the diluent administration means and/or transport system.

A further aspect of the invention comprises a kit, which comprises a device having a body in which is formed:
(i) a sample entry well location comprising means for engaging with a sample entry well;
(ii) an amplification well location comprising means for engaging with an amplification well;
(iii) a first channel linking the sample entry well when in position with the amplification well when in position;
(iv) a diluent well location comprising means for engaging with a diluent well, which well may be in a sealed configuration;
(v) a second channel linking the diluent well when in position and in an unsealed configuration, with the amplification well when in position;
(vi) a third channel extending from the amplification well when in position; and
(vii) a lateral flow device arranged to receive sample from the third channel and detect the target nucleic acid therein;
the kit further comprising a sample entry well positionable at the sample entry well location, an amplification well positionable at the amplification well location; and a diluent well positionable at the diluent well location, the well being sealed and openable to an unsealed configuration.

Embodiments of the kit are also contemplated in which one or more of the sample entry well, amplification well and/or diluent well are formed as an integral part of the device, with the sample entry well location comprising a sample entry well and/or the amplification well location comprising an amplification well and/or the diluent well location comprising a diluent well. Therefore, the kit may comprise a device as described herein with none, or one or more or all, of the sample entry well, amplification well and/or diluent well formed as an integral part of the device, with any non-integral wells being provided separately, either as a part of the same kit, or provided in separate packaging from the remainder of the kit.

In a preferred embodiment, the kit comprises a device having a body in which is formed:
(i) a sample entry well location comprising a sample entry well;
(ii) an amplification well location comprising means for engaging with an amplification well;
(iii) a first channel linking the sample entry well with the amplification well when in position;
(iv) a diluent well location comprising means for engaging with a diluent well, which well may be in a sealed configuration;
(v) a second channel linking the diluent well when in position, when in an unsealed configuration, with the amplification well when in position;
(vi) a third channel extending from the amplification well when in position; and
(vii) a lateral flow device arranged to receive sample from the third channel and detect the target nucleic acid therein;
the kit further comprising an amplification well positionable at the amplification well location and a diluent well positionable at the diluent well location, the well being sealed and openable to an unsealed configuration.

The amplification well and/or the diluent well may be provided as an integral part of the kit, or may be provided separately.

In another embodiment, the kit comprises a device having a body in which is formed:
(i) a sample entry well location comprising a sample entry well;
(ii) an amplification well location comprising an amplification well;
(iii) a first channel linking the sample entry well with the amplification well;
(iv) a diluent well location comprising means for engaging with a diluent well, which well may be in a sealed configuration;
(v) a second channel linking the diluent well when in position, when in an unsealed configuration, with the amplification well;
(vi) a third channel extending from the amplification well; and
(vii) a lateral flow device arranged to receive sample from the third channel and detect the target nucleic acid therein;
the kit further comprising a diluent well positionable at the diluent well location, the well being sealed and openable to an unsealed configuration. In any embodiment of the kit, the device may further comprise a sealing film extending across the entry to the second channel, positioned at the diluent well location. Alternatively or additionally, it may further comprise a sample entry well lid as described above. The device may additionally comprise an air vent at the diluent well location, which is a vent between the diluent well location and a void within the device, as discussed elsewhere herein.

In all embodiments of the kit, the sample entry well has a first volume, the amplification well has a second volume less than or the same as the first volume and the diluent well has a third volume greater than the second volume.

The device, apparatus, kit and combinations of the invention give rise to a useful and easy to operate means of carrying out nucleic acid amplification and detection. By storing reagents required for the process in closed wells in the device and making the device disposable, contamination risks are minimised.

In a further aspect, the invention provides a method for carrying out an assay to detect a nucleic acid in a sample, the method comprising adding a sample to a device according to the invention, loading the device into apparatus according to the invention and causing the apparatus to carry out a nucleic acid amplification and detection reaction therein, reading the results from the LFD. For example, the method may comprise adding a sample to the sample entry well and transferring it to the amplification well by means of closing the sample entry well lid, subjecting the amplification well to conditions under which a nucleic acid amplification reaction occurs, thereafter transferring diluent present in the diluent well to the amplification well, by opening the diluent well, to cause the contents to flow along the third channel to the lateral flow device and thereafter reading the results from the lateral flow device.

The method may comprise a step of engaging a sealed diluent well with the remainder of the device at the diluent well location. This may comprise initially non-sealingly engaging the well with the device at the diluent well location, subsequently sealingly engaging the well with the device and opening the well. The method may also comprise a step of moving an air vent, when present, from an open to a closed configuration.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Preferred features of each aspect of the invention may be as described in connection with any of the other aspects. Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWINGS

The invention will now be particularly described by way of example with reference to FIGS. 1-7 in which:

FIGS. 4B, 4C and 4D show detailed views of the diluent well and an embodiment of the air vent;

FIG. 1 shows the exterior of a device 1 according to the invention. This view shows the exterior housing 5 comprising upper and lower portions 10 and 15, respectively. A window 20 through which the LFD can be viewed is formed within the upper portion 10 of the housing 5. This view of the device shows a lid 25 which sits over a sample entry well, not visible in FIG. 1, the lid 25 being shown in the closed configuration. The lid 25 is joined to the housing by a hinge 30, held in place between the upper and lower portions 10 and 15 of the housing 5.

FIG. 1 further shows a diluent well 35 resiliently clipped within a diluent well dock 40, formed by a circular ridge located on the upper surface of the upper potion 10 of the exterior housing. The diluent well 35 comprises a button portion 45; a spike internally protrudes downwardly from the underside of this region (not shown) such that, if a user depresses the button portion 45 towards housing 5, the spike pierces a film (unseen) which sits under the diluent well, so that diluent contained within the diluent well 35 is released into channels within the device.

FIG. 1 also shows a protruding nose section 50 which comprises an amplification spigot 55 which protrudes downwardly from the nose section 50 and which is engageable with an amplification well, not shown in this Figure. The device is engageable with processing apparatus (not shown here) which comprises thermal cycling equipment, which can cause the contents of the amplification well, when engaged, to be processed through a cycle of temperature changes which may be required to facilitate a nucleic acid amplification reaction. Also visible in this view of the nose section 50 are the first channel 60 (linking the sample entry well with the amplification well when it is attached to the spigot), the second channel 65 (linking the diluent well 35 with the amplification well) and the third channel 70 (linking the amplification well with the mixing well, unseen in FIG. 1). Although channels 60, 65 and 70 are shown in FIG. 1 as being visible, for the purposes of illustration, all of the channels and the well are closed from the external environment by a transparent or opaque upper surface or film across the nose section 50.

FIG. 2 shows the device of FIG. 1 in exploded form, the overall body of the device being formed by upper 10 and lower 15 portions of the exterior housing 5 and a central layer 12. An upper film layer 84 is shown, which forms a layer across the top surface of central layer 12. Likewise, a lower film layer 86 is also shown.

Figure 1:
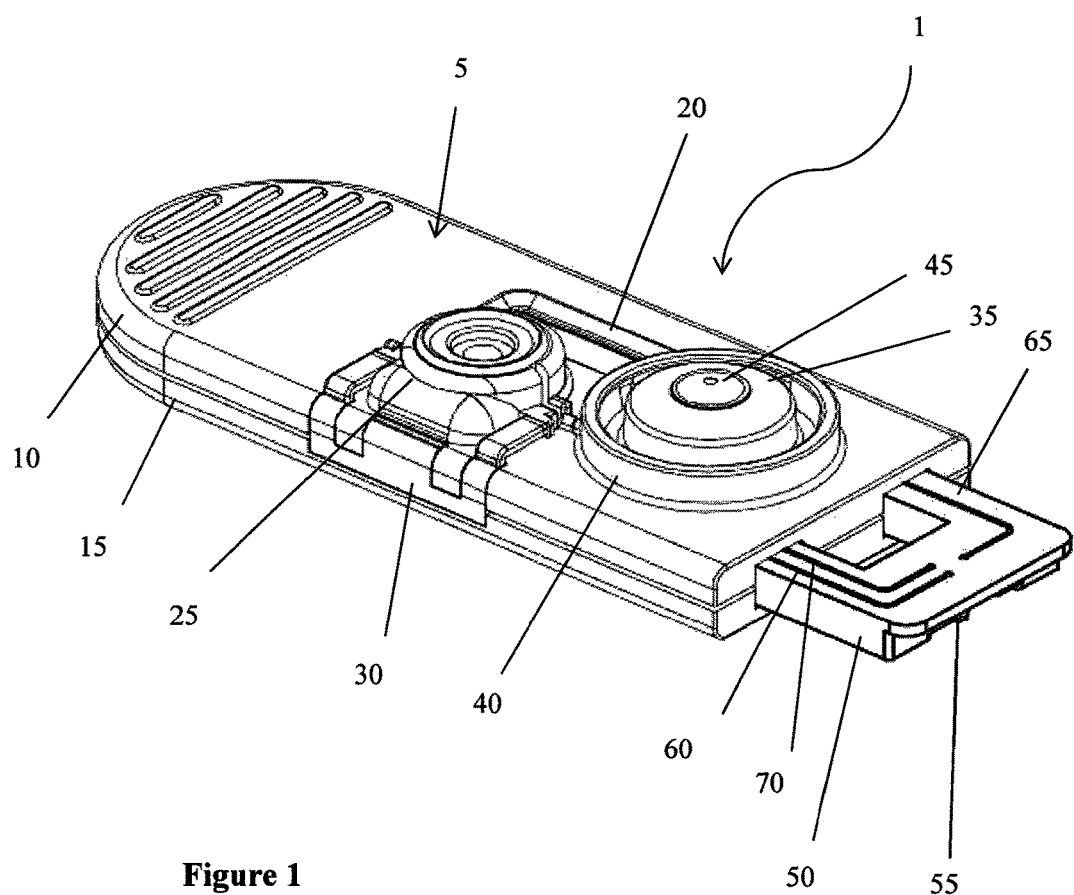
FIG. 1 shows the exterior of a device according to the invention.

The upper portion 10 of the exterior housing comprises the LFD viewing window 20 and the upper portion of sample entry well 22, as well as the diluent well dock 40. The diluent well 35 is provided as a separate consumable portion which may be resiliently clipped onto the body of the assembled device by engagement with the well dock 40. An annular channel 37 surrounding diluent well 35 may allow an additional tool, such as means within the processing apparatus, to engage with the diluent well 35 and press it further into engagement with the well dock 40. The button portion 45 is shown, from which a spike protrudes inside the diluent well 35, as explained above. A film 47 seals the diluent well 35 until it is opened by depressing the button portion 45 so that the spike (unseen) pierces the film 47. The diluent well also comprises a gasket 36 which is located on the exterior surface of the film 47 and, when the diluent well is engaged in the well dock 40, makes contact with the upper film layer 84 at the diluent well location mentioned below.

The upper and lower portions 10 and 15 of the housing 5 encase the central layer 12 of the device, an end region (indicated in FIG. 2 as A) of which protrudes from the housing 5 to form nose section 50 (as labelled in FIG. 1) when the device is assembled. Various channels and openings are formed in the material of the central layer 12. Recess 23 of the sample entry well 22 forms a lower chamber of the sample entry well, from which channel 60 extends to link lower chamber 23 of sample entry well 22 to the amplification well 56 via the spigot 55. A diluent receiving funnel 67 is linked to the amplification well by the channel 65. The amplification well is linked to the mixing well 75 by the channel 70. The aperture labelled 20b is the lower portion, formed in central layer 12, of LFD viewing window 20. The LFD 80 is linked to the mixing well 75 by a wicking material 79 which sits under the central layer 12. Also shown in FIG. 2 is the diluent well location (indicated by the dotted circle B), which is located on the central layer 12 under the diluent well dock 40. This is the region of the central layer 12 which, when the device is assembled, is located directly under the aperture formed by the diluent well dock 40 in upper portion 10. It comprises diluent receiving funnel 67 and the air vent channel 82 and separating wall 83, as described further below.

In use, when the button portion 45 of the diluent well 35 is depressed so that the film 47 is pierced by the spike, diluent from within the diluent well 35 moves into the channel 65 via the diluent receiving funnel 67 and then on through the spigot 55 to the amplification well 56, when engaged with the spigot 55. Continued depressing of the button portion 45 causes most of the diluent contained in the diluent well 35 to follow this path, in turn causing the contents of the amplification well to flow on through channel 70 and into the mixing well 75, when the lid 25 is in the closed configuration so that channel 60 is sealed.

FIG. 2 also shows a lid 25 which comprises a hinge 30 which joins the lid 25 to a lip 32 which can be located in aperture C in lower portion 15 of the housing 5 and gripped between upper portion 10 and lower portion 15 when the housing 5 is assembled. The lid has a bung 27 extending from its underside and an external surface 28 which may be contacted by a user to close the well. An O-ring 29 is located around the circumference of bung 27.

Figure 3A:
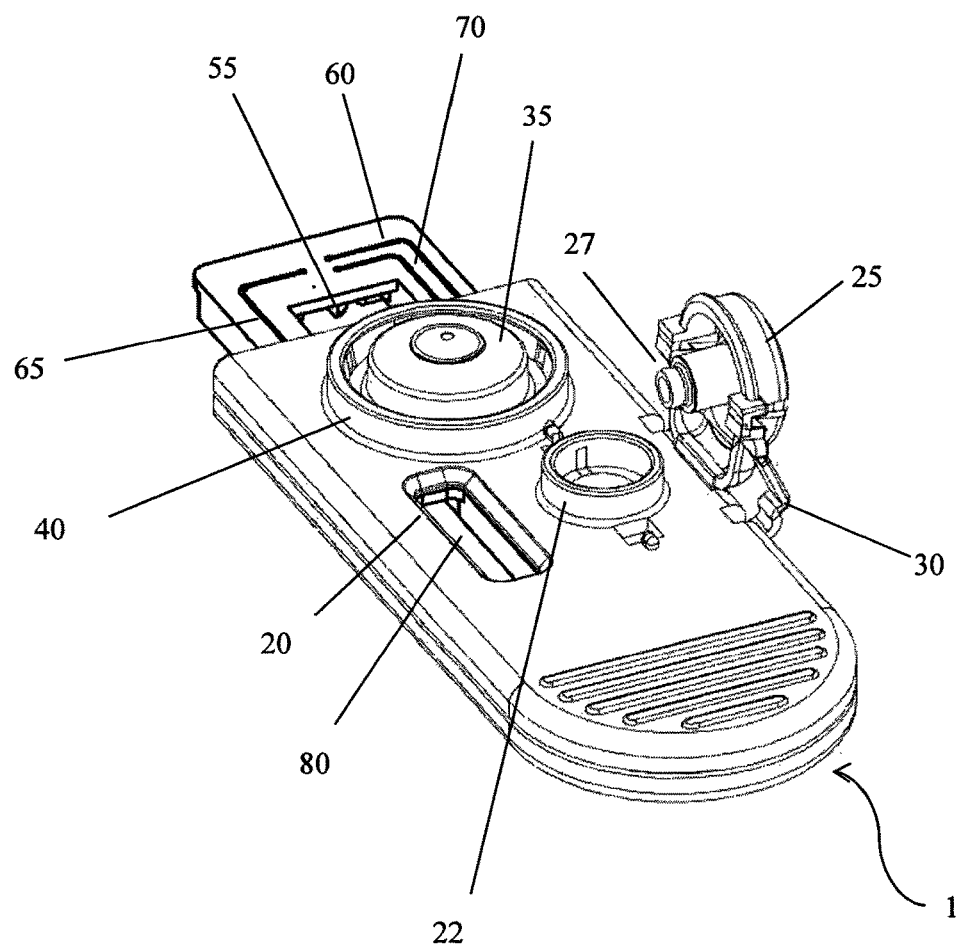
FIG. 3A shows the device with a sample entry well lid in open configuration.
Figure 3B:
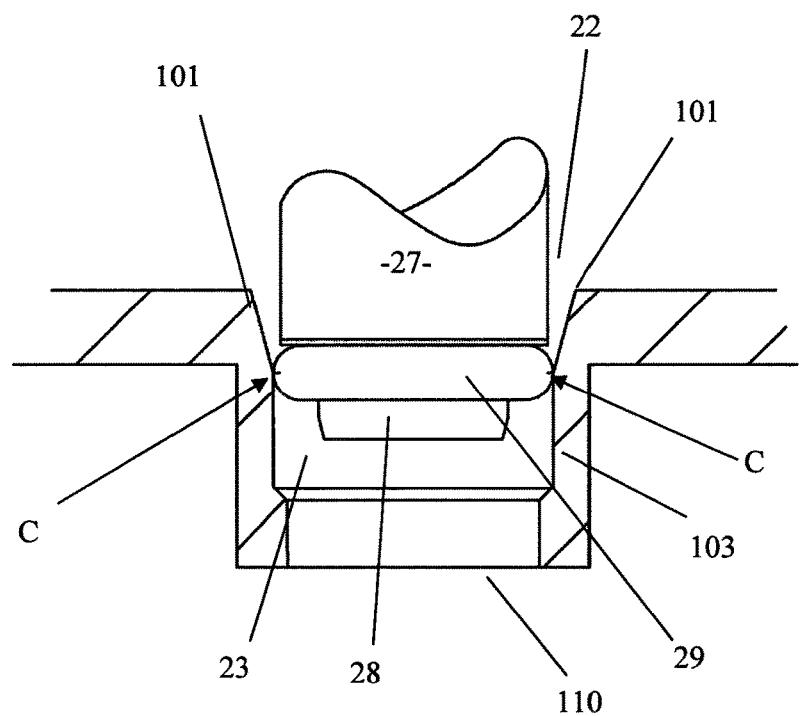
FIG. 3B shows a detailed cross-sectional view of a bung part of the lid making sealing contact with the lower chamber of the sample entry well.

FIG. 3A shows an alternative view of the device 1 with the lid in the open configuration. FIG. 3B shows this arrangement in more detail. The bung 27 has a blunt end 28 and comprises the O-ring 29 formed around the circumference of the bung 27. In this Figure, the bung 27 is located within the sample entry well 22 which comprises tapered shoulder side walls 101 and vertical side walls 103 which serve to engage the bung 27 with the lower portion 23 of the sample entry well 22. The O-ring 29 of the bung forms a sealing contact with the sample entry well 22 at points C. The channel entry (not shown) for channel 60, linking the sample entry well 22 with the amplification well via the spigot 55, is formed in the base 110 of the lower portion 23 of the sample entry well 22.

Figure 2:
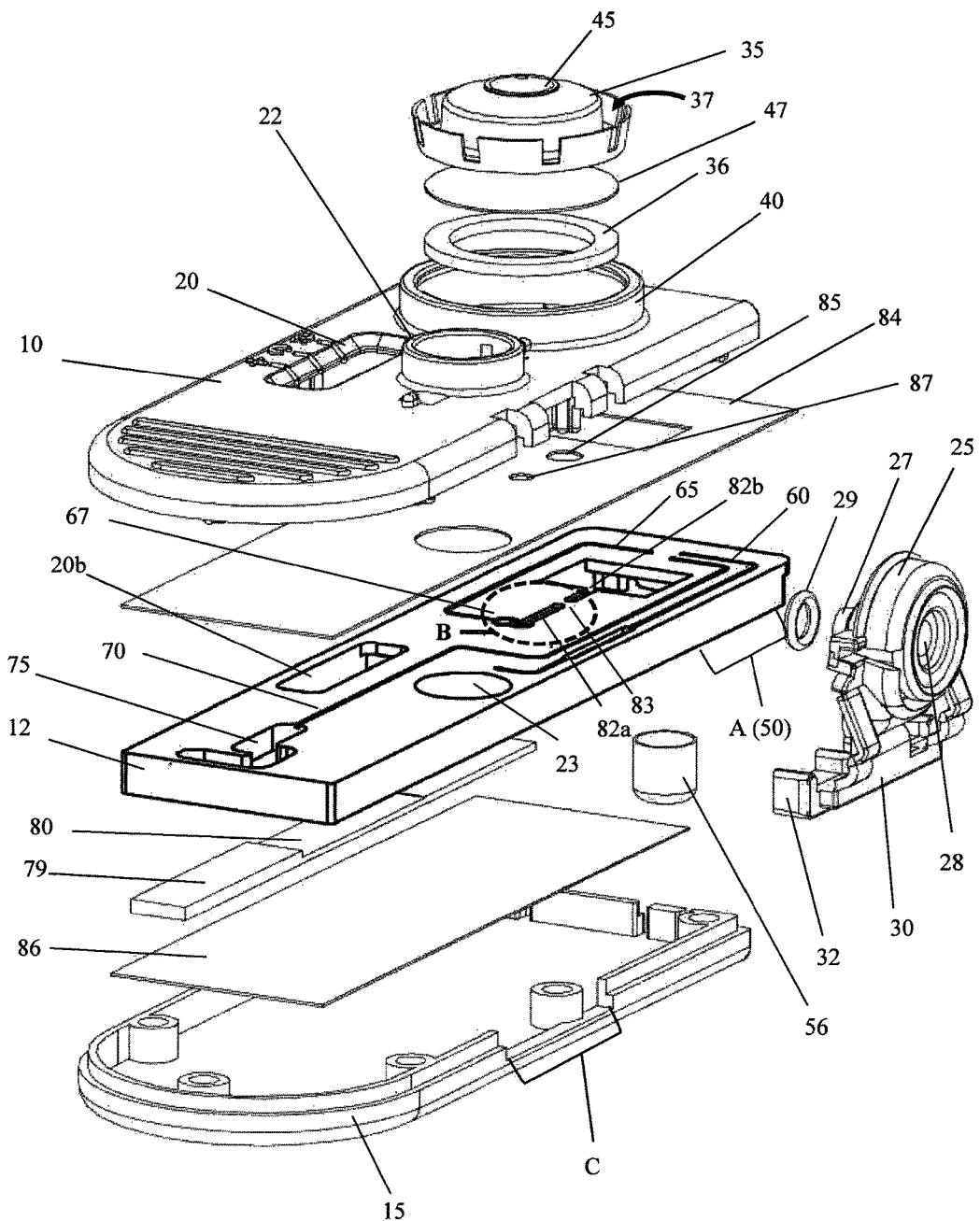
FIG. 2 shows an exploded view of the parts forming the device of FIG. 1.
Figure 3C:
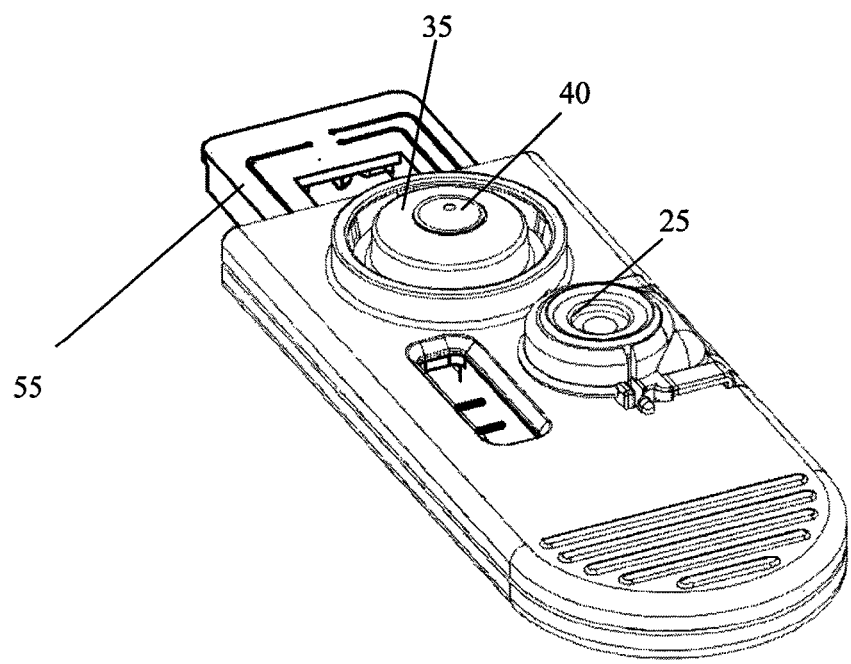
FIG. 3C shows the device with the lid in closed configuration.
Figure 3D:
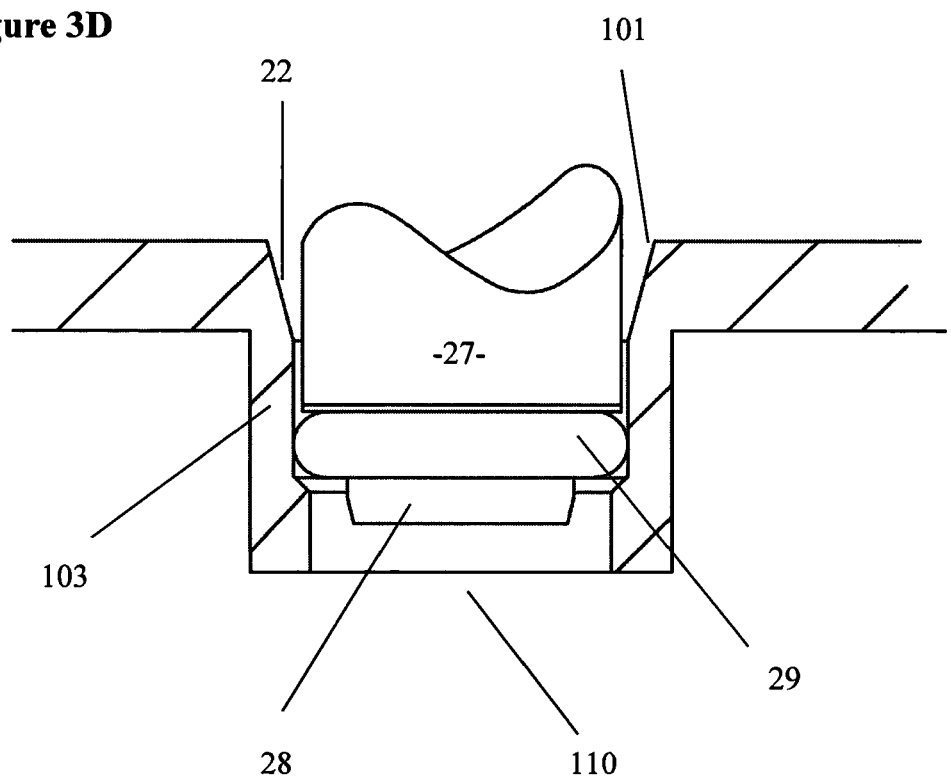
FIG. 3D shows detailed cross-sectional view of the bung part of the lid in the fully closed configuration, with liquid contents of the lower chamber sample entry well having been forced into the first channel.

FIG. 3C shows the device in FIG. 1 with the lid in the closed configuration. FIG. 3D shows the bung 27 fully depressed into the sample entry well 22, with the blunt end 28 of the bung 27 adjacent the base 110 of the sample entry well 22. The sealing contact formed by the O-ring 29 with the side walls 103 of the lower portion 23 of the sample entry well 22 has caused liquid contained within the lower portion 23 to be forced through the first channel entry and on through channel 60 into amplification chamber 55. Liquid sample which was contained in the other part of the sample entry well 22 (i.e., not in the lower portion 23) has been accommodated within the remainder of sample entry well 22 without leakage or splashing from the device, because the external dimensions of the bung 27 are less than the internal dimensions of the upper part of the sample entry well 22.

Figure 4A:
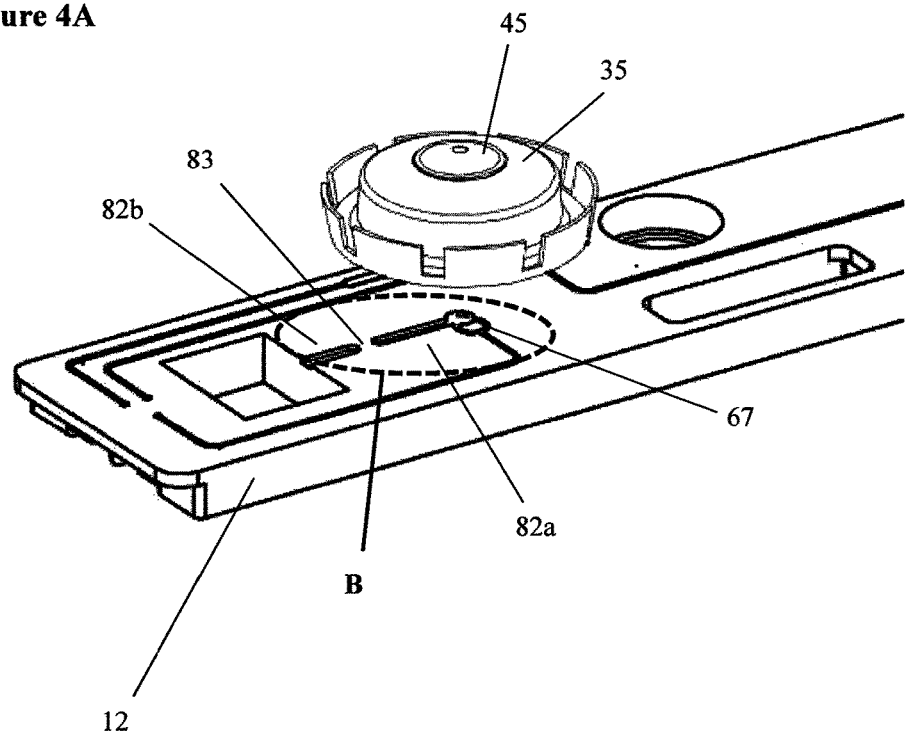
FIG. 4A shows a view of a central portion of the device and the relative positioning of the diluent well.
Figure 4B:
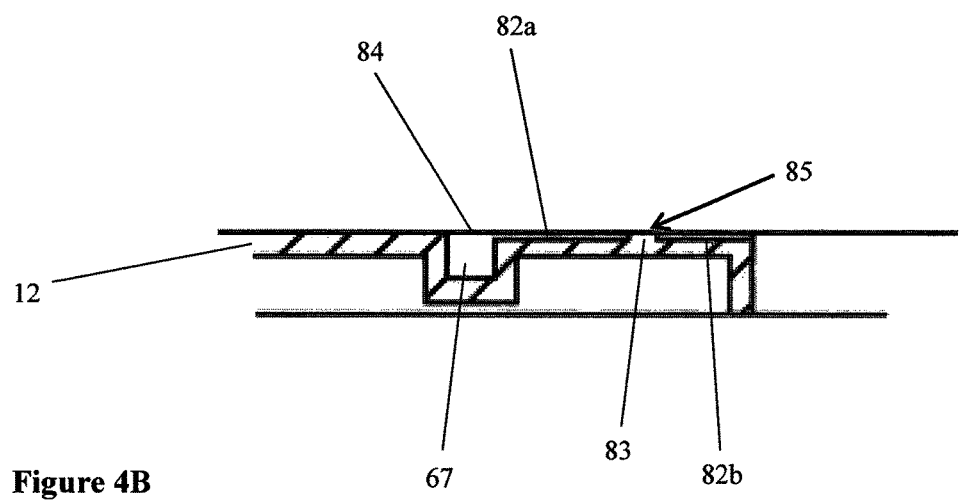

FIG. 4 shows one embodiment of the air vent feature in more detail. In FIG. 4A, the central layer 12 of the device is figuratively shown in the absence of the upper and lower portions of the housing, with the diluent well location shown as B. This is the region of the central layer 12 which sits below the diluent well dock 40 (formed in the upper portion 10 of the housing, not shown in this Figure), i.e., the region B sits under the diluent well 35 when it is engaged with the device. An air vent channel 82 extends from a position within region B to the exterior of the device and is connected to (i.e., in flow communication with) the diluent receiving funnel 67, which is the entry opening of channel 65. The two portions 82a and 82b of the air vent channel are separated by wall 83, formed by the material of the central layer 12. As shown in FIGS. 4B, 4C and 4D, a central layer film 84 sits across the upper surface of the central layer 12 of the device, a hole 85 being formed in the film above wall 83 (see also FIG. 2). A deformable foam gasket 36 is positioned on the underside of diluent well 35 and, when the well is placed in position over region B by engagement with diluent well dock 40, the gasket 36 covers the hole 83, but not with such force as to form a seal against wall 83 (i.e., air may move between the wall 83 and the gasket 36). This covers over the hole so as to link air vent channel portions 82a and 82b to form a channel 82 through which air emerging through channel 65 and diluent well funnel 67 can escape. Such movement of air through the system (as denoted by the dotted line in FIG. 4C) is caused when liquid sample is forced through channel 60 to the amplification well by the closing of lid 25.

When diluent well 35 is further forced into engagement with the diluent well dock 40, by the action of pressing down on annular channel 37 of the diluent well 35, for example by engagement of means within the processing apparatus, gasket 36 is pushed into sealing engagement with wall 83, so that the air vent is closed. Therefore, diluent forced into the diluent receiving funnel 67 proceeds into channel 60, on to the amplification well and from there through channel 70 to mixing well 75. The film 84 may be pre-perforated in the region of diluent receiving funnel 67 (for example, aperture 87 as shown in FIG. 2), or alternatively the spike of the diluent well 35 may pierce the central layer film 84 to allow diluent to emerge from diluent well 35 into diluent receiving funnel 67.

FIG. 5 shows an alternative embodiment of the air vent feature in more detail. In this Figure, the central layer 12 of the device is shown with the lower portion 15 of the housing in place. The central layer 12 is covered with an upper sealing film 84 and a lower sealing film 86. A void 90 is present between the material forming the central layer 12 and the lower sealing film 86.

Figure 5A:
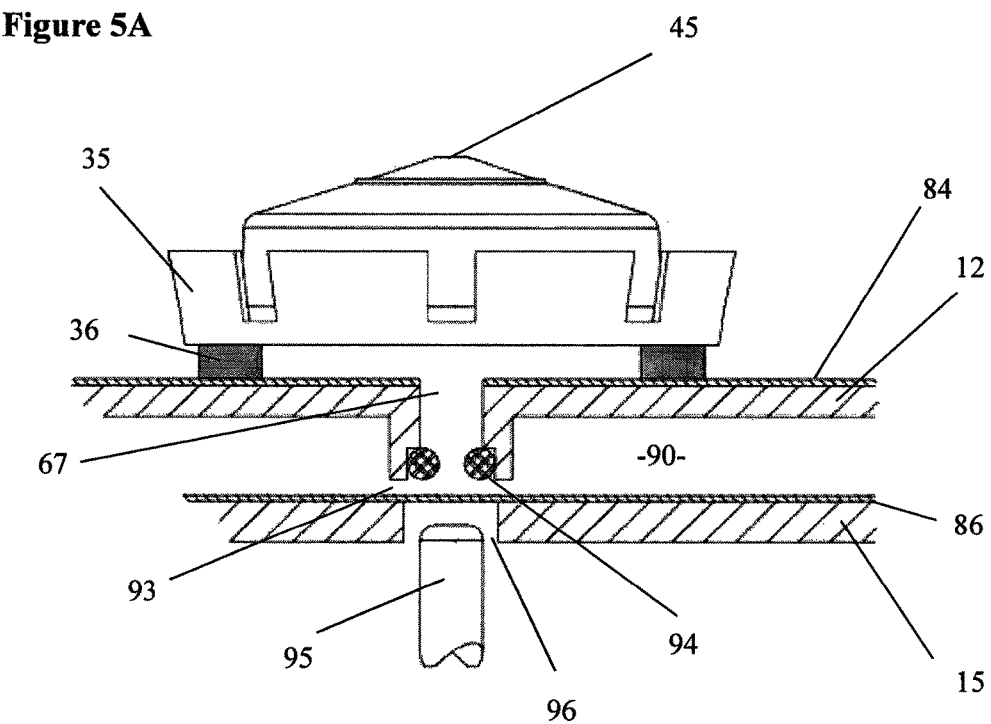
FIG. 5 shows an alternative arrangement for the air vent.

FIG. 5A shows a diluent well 35 clipped in place at the diluent well location. It comprises a deformable lower foam gasket 36, which makes contact with the material of the upper film 84 across the central layer 12 at the diluent well location. The diluent well 35 sits above the diluent receiving funnel 67 which forms the entry to the second channel. At the base of the receiving funnel 67 is an air vent 93 which provides flow communication between the receiving funnel 67 and the void 90. An O-ring 94 sits within the base of the receiving funnel 67, the O-ring comprising a central aperture through which fluid such as air may pass when the air vent is in the open configuration, as shown in FIG. 5A.

Figure 5B:
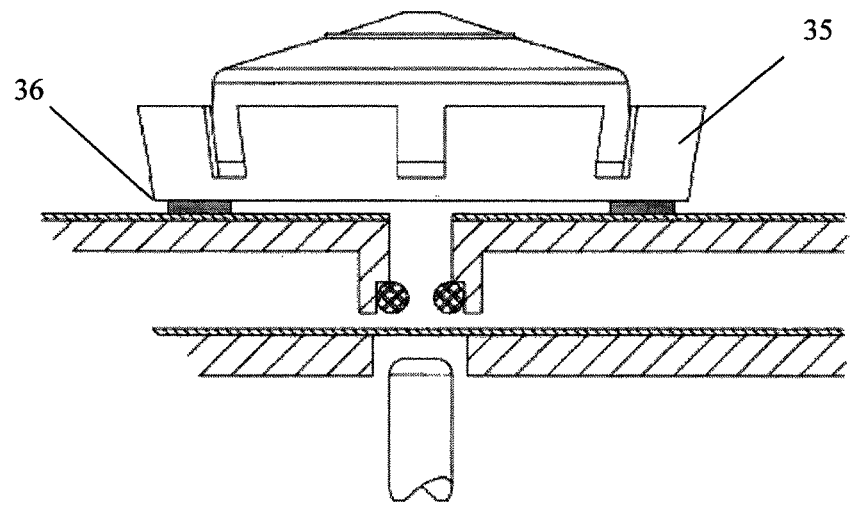

FIG. 5B shows the diluent well 35 pressed into full sealing engagement with the device, with the foam gasket 36 having being compressed. The diluent well, whilst still closed, is now in sealing engagement with the device as a whole. During compression of the gasket 36, the volume of air contained under it is able to escape into the void 90 via the air vent 93.

The O-ring 94 is then moved to a closed configuration by actuation of a sealing member, which in this exemplified embodiment is a pin 95 which is a part of the apparatus with which the device is engaged. The apparatus also facilitates heating/cooling cycles required for the amplification reaction to take place and the opening of the diluent well in due course. As shown in FIG. 5C, the pin 95 extends through a hole 96 formed, in the lower portion 15 of the housing, immediately underneath the air vent 93. Despite the hole 96, the interior of the device is sealed from the outer atmosphere by the presence of the lower sealing film 86 disposed between the air vent and the hole 96. The pin 95 makes contact with the film 86 covering the hole 96. Since the film is flexible, the pin is able to continue upwards to make contact with the O-ring 94. Upwards pressure on the O-ring 94 provides a seal within the air vent 93 such that it is in a closed configuration, as shown in FIG. 5C.

When the button portion 45 of the diluent well 35 is depressed, the film 47 (not shown) across the mouth of the diluent well 35 is pierced by the downwardly protruding spike (not shown) within the well, as is the upper sealing film 84 above the diluent receiving funnel 67. Diluent may then pass via the diluent receiving funnel 67 into the second channel and on to the amplification well, "flushing" the contents of the amplification well on towards the mixing well and, ultimately, the LFD.

Figure 6:
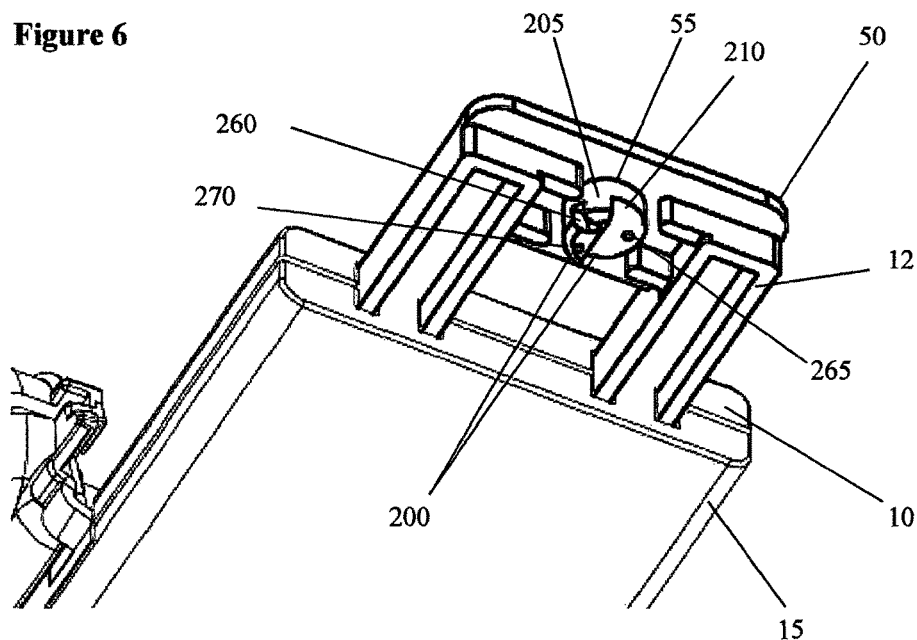
FIG. 6 shows an underside view of an amplification spigot.

FIG. 6 is an underside view of the amplification spigot 55. It is generally cylindrical in shape, having a circular exterior wall 200 which can frictionally engage with the interior wall of an amplification well which may be positioned over the spigot by a user, or provided to the user already positioned over the spigot. Alternatively, the amplification well may be formed as an integral part of the device, with the spigot 55 extending into the well. The spigot 55 is not uniformly cylindrical in shape, but comprises a longer half portion 205 and a shorter half portion 210. In the material of the longer half portion 205 are formed apertures 260 and 270 which are the exit from channel 60 and the entrance to channel 70, respectively. In the material of the shorter half portion 210 is formed aperture 265 which is the exit from channel 65. The aperture 260 is formed as a channel or notch in the side wall 200 of longer half portion 205.

Figure 7:
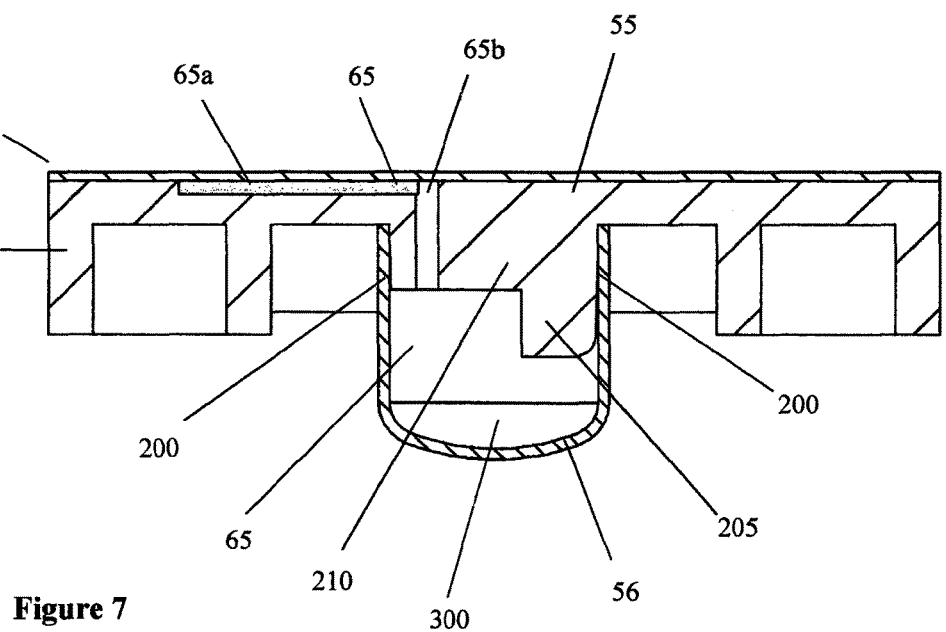
FIG. 7 is a cross-sectional view of an amplification well engaged with the amplification spigot.

FIG. 7 is a cross-section through spigot 55 (bisecting channel 65) when the amplification well 56 is engaged with it, at a time point after liquid sample which has been transferred to the amplification well 56 via channel 60 and aperture 260, by the action of closing lid 25, but before diluent has been dispensed into the device. The Figure shows channel 65 formed as a groove portion 65a and a downwardly directed tube portion 65b in the material of the central layer 12. Film 84 covers the top surface of the central layer 12. The aperture 265 is the exit opening from channel 65, the aperture 265 being formed in the shorter half portion 210 of the spigot. Channels and apertures in longer half portion 205 are not shown because of the orientation of the cross section. The interior wall of the amplification well 56 is frictionally engaged with the exterior wall 200 of the spigot 55. Liquid sample is indicated in FIG. 7 as 300.

Where the amplification well is not formed as a separate module but is, instead, a unified part of the device 1, there may, of course, not be a separate spigot, although, as mentioned, there may be an equivalent feature extending into the well. In any case, a similar arrangement of the entry and exit aperture 260, 265 and 270 will preferably be provided, particularly with apertures 260 and 270 being formed in a region close to the base of the amplification well, aperture 265 being formed in a region further away from the base of the well. The relative arrangement of these apertures has been found by the inventors to promote mixing of fluids within the device and to avoid the formation of air bubbles which might prevent proper transfer of liquids though the various channels and wells of the device and on to the LFD.

Referring to all of the Figures, when the device is in use, the diluent well 35 may initially be placed in position in diluent well dock 40 and the amplification well engaged with amplification spigot 55. The sample is added to sample entry well 22 by a user and the lid 25 is closed, perhaps manually by a user. Alternatively, the device is positioned in an apparatus and the closing of lid 25 is effected automatically by the apparatus. The closing of the lid 25 forces the bung 27 into sealing engagement with the walls of the lower portion 23 of the well 22, thereby moving liquid sample into channel 60 towards the spigot 55. Liquid emerges through channel 60 from aperture 260 into the amplification well and, because of the shape of aperture 260, is delivered onto a side wall of the amplification well, from where it flows down the side wall to the base of the well. Air from the amplification well and channel 60 can escape through aperture 265 and channel 65 and out through the air vent channel 82 in region B. The device is engaged in the processing apparatus such that the annular channel 37 surrounding the diluent well 35 is engaged with a hollow cylindrical member of the apparatus, this having a circumference engageably compatible with the circumference of the annular channel. This cylindrical member can force the diluent well 35 deeper into the dock 40 and causing gasket 36 to form a seal with the surface of the diluent well location, in one embodiment against wall 83 so that air vent 82 is closed. Alternatively, with reference to FIG. 5, a seal is formed by compression of gasket 36 and the apparatus extends the pin 95 to contact the O-ring 94, to close the air vent 93. The device also engages with heating means in the apparatus and the amplification reaction is carried out. At the end of the reaction, the button 45 of the diluent well 35 is depressed, by a movable plunger which is part of the apparatus. The accuracy of the volume of diluent dispensed is controlled by the combination of the volume and dimensions of the diluent well and the pre-calculated and determined extent of travel of the movable plunger. Diluent is forced through diluent receiving funnel 67, on through channel 65 and into the amplification well via aperture 265 in spigot 55. The volume of diluent exceeds the volume of the amplification well, so that liquid in the amplification well is pushed ahead of the diluent liquid, through aperture 270 into channel 70 and on to mixing well 75 where the liquids mix, before transferring to the LFD 80. The liquid in the amplification well is not pushed into aperture 260 because channel 60 and sample entry well 22 are sealed by the engagement of lid 25.

The invention claimed is:

1. A device for carrying out an assay to detect a target nucleic acid in a sample, the device comprising a body in which is formed:
   a) a sample entry well location comprising a sample entry well, the sample entry well having an overall volume, and the sample entry well including a first chamber defining a first partial volume of the sample entry well, and the sample entry well including a second chamber defining a second partial volume of the sample entry well, with the first chamber and the second chamber in flow communication with one another and collectively defining the overall volume of the sample entry well, wherein the first chamber is positioned below the second chamber;
   b) an amplification well location comprising an amplification well or means for engaging with an amplification well, the amplification well having a volume less than or the same as the overall volume of the sample entry well and in which a nucleic acid amplification reaction of the target nucleic acid may be effected;
   c) a first channel linking the sample entry well with the amplification well;
   d) a diluent well location comprising a diluent well or means for engaging with a diluent well, the diluent well being sealed, having a volume greater than the volume of the amplification well, and being openable to an unsealed configuration;
   e) a second channel linking the diluent well, when in an unsealed configuration, with the amplification well;
   f) a third channel extending from the amplification well;
   g) a lateral flow device arranged to receive sample from the third channel and detect the target nucleic acid therein; and
   h) a sample entry well closing lid, the closing lid including a protruding distal portion which is formed to have mating dimensions so as to be engageable with the first chamber of the sample entry well, the closing lid having an open configuration in which the protruding distal portion is not located in the first chamber or the second chamber of the sample entry well, and a closed configuration in which the protruding distal portion engages the first chamber of the sample entry well, wherein, in use, as the closing lid is moved from the open configuration to the closed configuration, a pre-determined volume of liquid contained in the first chamber of the sample entry well is moved to the amplification well via the first channel.

2. The device of claim 1 wherein the sample entry well is linked to the amplification well directly by the first channel with no intervening wells and/or channels.

3. The device of claim 1 wherein the diluent well is formed as a separate sealed well engageable with the remainder of the device to form part of the device.

4. The device of claim 1 wherein the amplification well location comprises a protrusion extending from the body of the device into the amplification well when present, the protrusion comprising an exit aperture for the first and second channels and an entry aperture for the third channel.

5. The device of claim 4 wherein the first channel exit aperture and the third channel entry aperture are formed in a region of the protrusion distal from the body of the device.

6. The device of claim 4 wherein the first channel exit aperture is at least partially formed in a side wall of the protrusion.

7. The device of claim 1 wherein the amplification well is formed as a separate well engageable with the remainder of the device at the amplification well location.

8. The device of claim 1 wherein the first channel extends from a base region of the sample entry well.

9. The device of claim 1 comprising an air vent in an open configuration, moveable to a closed configuration, such that the air vent in the open configuration provides a flow communication between the second channel and a void in the device.

10. The device of claim 1 wherein, when the diluent well forms part of the device and/or is engaged with the device, liquid contents of the diluent well are sealed within the diluent well which may be opened to dispense the contents into the second channel.

11. The device of claim 1 wherein the amplification well is preloaded with at least one reagent suitable for carrying out a nucleic acid amplification reaction.

12. The device of claim 1, further comprising a mixing well connected to the amplification well by means of the third channel, wherein the third channel is arranged such that contents of the amplification well may be transferred to the mixing well, the lateral flow device being arranged to receive sample from the mixing well and detect the target nucleic acid therein.

13. The device of claim 12 wherein the mixing well is non-straight or serpentine in shape.

14. The device of claim 1, wherein the protruding distal portion of the closing lid is a bung, with an O-ring formed around the circumference of the bung that forms a sealing contact with the first chamber of the sample entry well.

15. The device of claim 1, wherein the closing lid is mounted for rotation relative to the sample entry well between the open configuration in which the protruding distal portion is not located in the first chamber or the second chamber of the sample entry well, and the closed configuration in which the protruding distal portion engages the first chamber of the sample entry well.

16. A kit comprising the device of claim 1 and a sealed diluent well, the device comprising a diluent well location which comprises means for engaging with a diluent well.

17. The kit of claim 16, and further comprising an amplification well and a diluent well, the device comprising an amplification well location which comprises means for engaging with an amplification well and a diluent well location which comprises means for engaging with a diluent well.

18. An apparatus for carrying out a chemical or biochemical reaction, the apparatus comprising:
   a) a means for receiving the device of claim 1, the device comprising an amplification well and a diluent well; and
   b) a heating means arranged to controllably heat the amplification well so as to allow a chemical or biochemical reaction to be carried out therein.

19. A device for carrying out an assay to detect a target nucleic acid in a sample, the device comprising a body in which is formed:
- a) a sample entry well location comprising a sample entry well, the sample entry well having an overall volume, and the sample entry well including a first chamber defining a first partial volume of the sample entry well, and the sample entry well including a second chamber defining a second partial volume of the sample entry well, with the first chamber and the second chamber in flow communication with one another and collectively defining the first volume of the sample entry well, wherein the first chamber is positioned below the second chamber;
- b) an amplification well location comprising an amplification well or means for engaging with an amplification well, the amplification well having a volume less than or the same as the overall volume of the sample entry well and in which a nucleic acid amplification reaction of the target nucleic acid may be effected in the liquid phase;
- c) a first channel linking the sample entry well with the amplification well;
- d) a diluent well location comprising means for engaging with a diluent well, wherein the diluent well is formed as a separate sealed well engageable with the remainder of the device;
- e) a second channel linking the diluent well location with the amplification well;
- f) a third channel extending from the amplification well;
- g) a lateral flow device arranged to receive sample from the third channel and detect the target nucleic acid therein; and
- h) a sample entry well closing lid, the closing lid including a protruding distal portion which is formed to have mating dimensions so as to be engageable with the first chamber of the sample entry well, the closing lid having an open configuration in which the protruding distal portion is not located in the first chamber or the second chamber of the sample entry well, and a closed configuration in which the protruding distal portion engages the first chamber of the sample entry well, wherein, in use, as the closing lid is moved from the open configuration to the closed configuration, a predetermined volume of liquid contained in the first chamber of the sample entry well is moved to the amplification well via the first channel.

20. The device of claim 1, wherein the protruding distal portion of the closing lid is a bung, with an O-ring formed around the circumference of the bung that forms a sealing contact with the first chamber of the sample entry well.

21. The device of claim 19, wherein the closing lid is mounted for rotation relative to the sample entry well between the open configuration in which the protruding distal portion is not located in the first chamber or the second chamber of the sample entry well, and the closed configuration in which the protruding distal portion engages the first chamber of the sample entry well.

* * * * *